United States Patent
Basak

(10) Patent No.: US 10,557,129 B2
(45) Date of Patent: Feb. 11, 2020

(54) PEPTIDES DERIVED FROM HUMAN PCSK9 CATALYTIC DOMAIN AND USES THEREOF FOR PROMOTING LDL-R ACTIVITY

(71) Applicant: Pronasci Inc., Dollard-des-Ormeaux (CA)

(72) Inventor: Ajoy Basak, Ottawa (CA)

(73) Assignee: Pronasci inc., Montreal (CA)

( * ) Notice: Subject to any disclaimer, the term of this patent is extended or adjusted under 35 U.S.C. 154(b) by 0 days.

(21) Appl. No.: 15/547,277

(22) PCT Filed: Jan. 29, 2016

(86) PCT No.: PCT/CA2016/050080
§ 371 (c)(1),
(2) Date: Jul. 28, 2017

(87) PCT Pub. No.: WO2016/119067
PCT Pub. Date: Aug. 4, 2016

(65) Prior Publication Data
US 2018/0023071 A1  Jan. 25, 2018

Related U.S. Application Data

(60) Provisional application No. 62/109,790, filed on Jan. 30, 2015.

(51) Int. Cl.
| C07K 7/08 | (2006.01) |
| C12N 9/64 | (2006.01) |
| A61K 38/48 | (2006.01) |
| A61K 45/06 | (2006.01) |

(52) U.S. Cl.
CPC .......... *C12N 9/6454* (2013.01); *A61K 38/482* (2013.01); *A61K 45/06* (2013.01); *C12Y 304/21061* (2013.01)

(58) Field of Classification Search
None
See application file for complete search history.

(56) References Cited

FOREIGN PATENT DOCUMENTS

WO   WO-2010057242 A2 *  5/2010  ......... A61K 39/0012

OTHER PUBLICATIONS

Lammi, Carmen et al, "Lupin peptides lower low-density lipoprotein(ldl) cholesterol through an up-regulation of teh ldl receptor/sterol regulatory element binding protein 2 (srebp2) pathay at hepg2 cell line." J. Agr. Food Chem. (2014) 62 p. 7151-7159.*
Machine translation of WO 2010057242, 2010.*
Alghamdi et al.; "LDL-R promoting activity of peptides derived from human PCSK9 catalytic domain (153-421): Design, synthesis and biochemical evaluation", European Journal of Medicinal Chemistry, Jan. 12, 2015 (Jan. 12, 2015), vol. 92, pp. 890-907.
International Search Report of PCT/CA2016/050080; Gatineau; dated Apr. 21, 2016; McLean, Jeremy.

* cited by examiner

*Primary Examiner* — Fred H Reynolds
(74) *Attorney, Agent, or Firm* — Benoit & Cote, Inc.; Mathieu Miron

(57) ABSTRACT

The present invention provides compositions comprising an isolated or purified therapeutically effective hPCSK9 polypeptide derived from the hPCSK9 catalytic domain, and their use in methods of treating hypercholesterolemia.

13 Claims, 19 Drawing Sheets
Specification includes a Sequence Listing.

PEPTIDES DERIVED FROM HUMAN PCSK9 CATALYTIC DOMAIN AND USES THEREOF FOR PROMOTING LDL-R ACTIVITY

CROSS-REFERENCE TO RELATED APPLICATIONS

This application is a US National Phase application under 35 USC § 371 of PCT/CA2016/050080, filed Jan. 29, 2016, which claims priority from and the benefit of U.S. Provisional Application No. 62/109,790, filed Jan. 30, 2015, the specifications of which are hereby incorporated by reference in their entireties.

BACKGROUND

(a) Field

The subject matter disclosed generally relates to isolated or purified therapeutically effective hPCSK9 derived polypeptides. More specifically, the subject matter disclosed relates to isolated or purified therapeutically effective hPCSK9 polypeptides from its catalytic domain (aa153-421) of hPCSK9, and uses thereof (aa: Amino acid).

(b) Related Prior Art

Proprotein Convertase Subtilisin Kexin 9 (PCSK9) was first discovered in 2003 and was called Neural Apoptosis Regulated Convertase-1 (NARC-1). It is the 9th member of mammalian subtilase super family now collectively known as PCSK. The first 8 members of this family, PCSK1-8 have been implicated in the processing of a variety of inactive precursor proteins to generate functional and bioactive peptides, polypeptides and hormones that play important roles in maintaining growth, metabolism and overall general health, as well as a variety of illnesses. PCSK9 is unique in this respect since only very limited data is available about the proteolytic activity and its substrate. In fact its protease activity is not at all linked to its physiological action and biological activity. It acts primarily as a secreted soluble protein that mediates degradation of the membrane bound Low Density Lipoprotein receptor (LDL-R) by binding with its extracellular domain and targeting the receptor for degradation via rerouting to the lysosomal pathway.

LDL protein and its receptor LDL-R on plasma cell surface are the major carriers of cholesterol in the blood. LDL-receptors are particularly abundant in the liver, the primary organ responsible for removing excess cholesterol from the body. The number of LDL-receptors on the surface of liver cells determines how quickly cholesterol is removed from the bloodstream. Accumulation of LDL-Cholesterol (LDL-C) in the plasma is known to cause the formation of atherosclerotic plaque—a major risk factor of cardiovascular disease (CVD) which remains as the major killer worldwide particularly in western hemisphere. So hPCSK9 which is comprised of 12 exons that translate to 5 domains with 692 aa protein is considered as the third target gene besides Apo-B and LDL-R for cholesterol regulation. Following removal of signal peptide domain hPCSK9 is secreted as ~74 kDa full length protein which is autocatalytically cleaved at VFAQ$^{152}$↓SIP to generate ~14 kDa prodomain and ~60 kDa mature protein which remain strongly associated to one another. It is this complex that interacts and binds with the EGF-A domain of LDL-R leading to the ultimate degradation of latter and accumulation of LDL-C in the blood.

A large variety of PCSK9 mutations in human have been identified which cause increased (Gain of function mutation), decreased (Loss of function) or unaltered level of cholesterol in the serum. PCSK9 gain of function mutations lead to hypercholesterolemia and loss of function mutation leads to hypocholesterolemia. The two most profound gain of function mutations in hPCSK9 have been identified as Asp$^{374}$/Tyr and Arg$^{357}$/His. Interestingly these mutations are located within the catalytic domain (aa153-421) and the former variant is capable of binding to LDL-R with 25-fold stronger affinity leading to 23% decreased LDL-R and ~38% decreased level of LDL-R internalization [Caneron J, Holla O L, Rauheim T, Kulseth M-A, Berge K E, Leren T P. Effect of mutations in the PCSK9 gene on the cell surface LDL receptors *Hum Mol Genet.* 15(9):1551-1558, 2006] responsible for ultimate increase in serum LDL-C. This mutation has been identified in 3% of the population with Autosomal Dominant Hypercholesterolemia (ADH). On the other hand most loss of function mutations has been characterized in African Americans with low levels of circulating LDL-C. Such mutations have resulted in a 30% increase in LDL-R, a truly protective effect against hypercholesterolemia and cardiovascular diseases. The most extreme loss of function mutation Arg$^{46}$/Leu in the pro-domain, have resulted in ~42% decrease in LDL-C.

Very recently a novel loss of function mutation at the prodomain cleavage site of hPCSK9 (Gln$^{152}$/His) has been discovered in a French Canadian family. This mutation resulted in impaired processing (no autocatalytic processing) and secretion in cell culture resulting in circulating PCSK9 and LDL-C concentrations of 79% and 48%, respectively, compared with unrelated non-carriers. The clinical and biochemical studies involving hPCSK9 variants as well as PCSK9 knock out, knock down and over-expressed mice studies all confirmed the key role of PCSK9 in cholesterol regulation As a result it has been identified as an important target for development of non-statin alternative cholesterol lowering agents. Statins have long been recognized as effective cholesterol lowering agents which inhibit HMG-CoA reductase—a crucial enzyme in the liver responsible for cholesterol synthesis. Statins work quite well in lowering LDL-C in most patients but a few do not have a strong response to statin treatment. In addition they may cause (i) Cognitive problems (~2% patients), (ii) Increased risk of delirium in patients after surgery (up to 10% patients); (iii) Muscle pain/weakness & neuropathy; (1-5% patients), (iv) Elevation of liver enzymes Aspartate Aminotransferase (AST) and Alanine Aminotransferase (ALT) causing liver failure; (v) Increased risk of type 2 diabetes (~9% population); (vi) Increase in colorectal and prostate cancers particularly in obese men.

Due to these findings, interest has grown to develop inhibitors of PCSK9 as potential cholesterol reducing agents alternative to statins. Various approaches have been pursued that include delivery of single stranded anti-sense DNA, RNAi and specific antibody preferably monoclonal (mAb) of PCSK9. Significant progress has been accomplished with the development of several mAbs by major pharmaceutical companies that include Sanofi-Regeneron Pharmaceuticals (REGN727 or Alirocumab), Amgen company (AMG145 or Evolocumab), Pfizer (RN 316 or Bococizumab) and Lilly (LY3015014). The first two of these antibodies have been proved to be most successful in human clinical trials and may soon be approved by Food and Drug Administration (FDA) as first PCSK9 targeted cholesterol lowering agents. Despite this success with mAbs, there is still a growing interest to develop small compound inhibitors of hPCSK9 which unlike the Abs are expected to be less expensive, more aqueous soluble, proteolytically & thermally stable as well as more bio-available. Currently only a limited number of data are available on small compound PCSK9 inhibitors. These include synthetic EGF-A peptide, Anexin-A2 and its derived peptides, PCSK9 prodomain derived peptides, the plant alkaloid barberine and the crude extract of *Moringa Oleifera* (59). More recently using phage-display library, a small linear peptide called Pep2-8 (13 mer long with sequence: Ac-TVFTSWEEYLDWV) (Ac=Acetyl) which structurally mimics EGF-A domain of LDL-R has been identified as the smallest PCSK9 inhibitor with $IC_{50}$~1.4-0.2 μM. Another study revealed that a peptide derived from EGF-A domain of LDL-R also exhibited potent PCSK9 inhibition.

The present invention concerns small molecule PCSK9 inhibitors based on peptides derived from its own catalytic domain (aa153-421) (FIG. 1) which has been shown by crystal structure [Piper D E, Jackson S, Liu Q, Romanow W G, Shetterley S, Thibault S T, Shan B, Walker N P. The crystal structure of PCSK9: A regulator of plasma LDL-cholesterol. *Structure* 15:545-552, 2007.] and other studies to bind to LDL-R responsible for latter degradation. It is possible that hPCSK9 catalytic domain may contain binding sites for both its own prodomain and the EGF-A domain of hLDL-R. A schematic diagram showing the proposed interactions and possible mechanism of PCSK9-mediated breakdown of LDL-R is presented in FIG. 2. A Previous studyreported data showing that two peptides of catalytic segment of hPCSK9 namely (aa181-200) and (aa368-390) exhibited modest LDL-R promoting effect when added exogenously to growing HepG2 cells. A more in depth analysis has been carried herein to identify specific segment/s of the catalytic domain of hPCSK9 (aa153-421) responsible for its interaction with LDL-R. Thus, according to an embodiment of the present invention, using a series of 51 peptides with partial overlapping sequences which cover the entire hPCSK9 catalytic domain, at least two segments in hPCSK9 catalytic domain were identified that significantly diminish LDL-R degradation when added exogenously to the culture medium of growing hepatic HepG2 cells. In the present study we describe the design, synthesis and comparative LDL-R regulating activities of these peptides under in vitro and cellular systems such as HepG2. The results obtained are presented herein.

Research in this field is gaining tremendous importance for designing new cholesterol lowering agents. In fact two monoclonal antibodies, AMG145 by Amgen Company and Fab (Fragment antibody called REGN727/SAR236553 by Regeneron and Sanofi Companies directed against PCSK9 functional activity have successfully passed all short term phase and clinical trial studies including humans and will soon become first PCSK9 based therapeutics for cholesterol control. Two additional antibodies called RN316 by Pfizer Company and LGT209 by Novartis Company have either completed or in the process of Phase-II trial. Despite these success stories, research is still ongoing for identification of small compound inhibitors of PCSK9, both peptide and nonpeptide origins because of the many reasons as outlined above, but very little data are currently available in this field.

SUMMARY

According to an embodiment, there is provided an isolated or purified therapeutically effective hPCSK9 polypeptide derived from one of the amino acid sequence SEQ ID NO: 54, SEQ ID NO: 55, and SEQ ID NO: 58.

The isolated or purified therapeutically effective hPCSK9 polypeptide may consist of the amino acid sequence of any one of SEQ ID NOS: 35 to 39, SEQ ID NOS: 42 to 47, and SEQ ID NO: 56.

The isolated or purified therapeutically effective hPCSK9 polypeptide may consist of the amino acid sequence of any one of SEQ ID NO: 36, SEQ ID NO: 37, SEQ ID NO: 42, SEQ ID NO: 43, SEQ ID NO: 47, SEQ ID NO: 56 or combinations thereof.

The isolated or purified therapeutically effective hPCSK9 polypeptide may consist of the combination of the amino acid sequence SEQ ID NO: 36 and SEQ ID NO: 37, SEQ ID NO: 36 and SEQ ID NO: 42 or SEQ ID NO: 36 and SEQ ID NO: 47.

According to another embodiment, there is provided an isolated or purified therapeutically effective hPCSK9 polypeptide having the amino acid sequence:

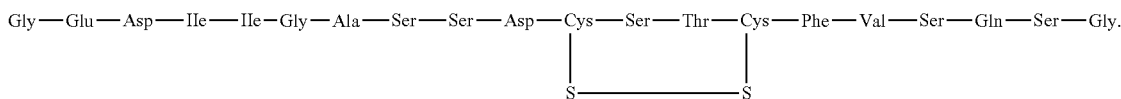

According to another embodiment, there is provided a pharmaceutical composition comprising a therapeutically effective amount of an isolated or purified therapeutically effective hPCSK9 polypeptide of the present invention, or combinations thereof, and a pharmaceutically acceptable carrier.

According to another embodiment, there is provided a method of preventing or treating hypercholesterolemia comprising administering to a subject in need thereof at least one of an isolated or purified therapeutically effective hPCSK9 polypeptide of the present invention, or combinations thereof, or a pharmaceutical composition of the present invention.

The method may comprise further administering a HMG-CoA reductase inhibitors (statin).

The HMG-CoA reductase inhibitors (statin) may be for administration before, at the same time or after said hPCSK9 polypeptide.

According to another embodiment, there is provided an isolated or purified therapeutically effective hPCSK9 polypeptide derived from one of the amino acid sequence SEQ ID NO: 54, SEQ ID NO: 55, and SEQ ID NO: 58 for preventing or treating hypercholesterolemia.

The isolated or purified therapeutically effective hPCSK9 polypeptide may consist of the amino acid sequence of any one of SEQ ID NOS: 35 to 39, SEQ ID NOS: 42 to 47, and SEQ ID NO: 56.

The isolated or purified therapeutically effective hPCSK9 polypeptide may consist of the amino acid sequence of any one of SEQ ID NO: 36, SEQ ID NO: 37, SEQ ID NO: 42, SEQ ID NO: 43, SEQ ID NO: 47, SEQ ID NO: 56 or combinations thereof.

The isolated or purified therapeutically effective hPCSK9 polypeptide may consist of the combination of the amino acid sequence SEQ ID NO: 36 and SEQ ID NO: 37, SEQ ID NO: 36 and SEQ ID NO: 42 or SEQ ID NO: 36 and SEQ ID NO: 47.

According to another embodiment, there is provided an isolated or purified therapeutically effective hPCSK9 polypeptide having the amino acid sequence:

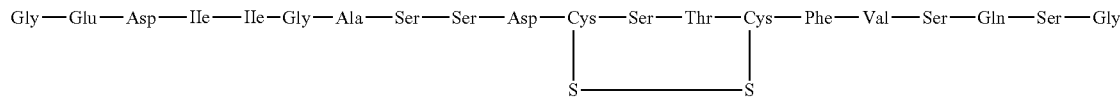

for preventing or treating hypercholesterolemia.

The isolated or purified therapeutically effective hPCSK9 polypeptide of the present invention may be for use with a HMG-CoA reductase inhibitors (statin).

The HMG-CoA reductase inhibitors (statin) may be for use before, at the same time or after said hPCSK9 polypeptide.

According to another embodiment, there is provided a pharmaceutical composition for use in preventing or treating hypercholesterolemia, comprising a therapeutically effective amount of an isolated or purified therapeutically effective hPCSK9 polypeptide of the present invention, or combinations thereof, and a pharmaceutically acceptable carrier.

The pharmaceutical composition may further comprise a HMG-CoA reductase inhibitors (statin).

The HMG-CoA reductase inhibitors (statin) may be for use before, at the same time or after said hPCSK9 polypeptide.

According to another embodiment, there is provided a use of an isolated or purified therapeutically effective hPCSK9 polypeptide derived from one of the amino acid sequence SEQ ID NO: 54, SEQ ID NO: 55, and SEQ ID NO: 58 for preventing or treating hypercholesterolemia in a subject in need thereof.

The isolated or purified therapeutically effective hPCSK9 polypeptide may consist of the amino acid sequence of any one of SEQ ID NOS: 35 to 39, SEQ ID NOS: 42 to 47, and SEQ ID NO: 56.

The isolated or purified therapeutically effective hPCSK9 polypeptide may consist of the amino acid sequence of any one of SEQ ID NO: 36, SEQ ID NO: 37, SEQ ID NO: 42, SEQ ID NO: 43, SEQ ID NO: 47, SEQ ID NO: 56 or combinations thereof.

The isolated or purified therapeutically effective hPCSK9 polypeptide may consist of the combination of the amino acid sequence SEQ ID NO: 36 and SEQ ID NO: 37, SEQ ID NO: 36 and SEQ ID NO: 42 or SEQ ID NO: 36 and SEQ ID NO: 47.

According to another embodiment, there is provided a use of an isolated or purified therapeutically effective hPCSK9 polypeptide having the amino acid sequence:

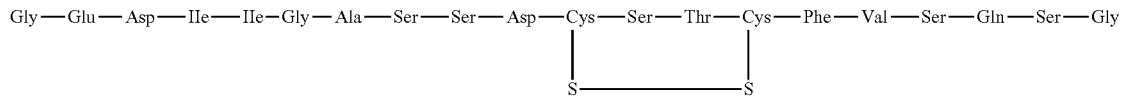

for preventing or treating hypercholesterolemia in a subject in need thereof.

The use may further comprise a HMG-CoA reductase inhibitors (statin).

The HMG-CoA reductase inhibitors (statin) may be for use before, at the same time or after said hPCSK9 polypeptide.

According to another embodiment, there is provided a kit for use for the prevention or the treatment of hypercholesterolemia in a subject in need thereof, the kit comprising:
  an isolated or purified therapeutically effective hPCSK9 polypeptide derived from one of the amino acid sequence SEQ ID NO: 54, SEQ ID NO: 55, and SEQ ID NO: 58; and
  instructions on how to use the kit.

The isolated or purified therapeutically effective hPCSK9 polypeptide may consist of the amino acid sequence of any one of SEQ ID NOS: 35 to 39, SEQ ID NOS: 42 to 47, and SEQ ID NO: 56.

The isolated or purified therapeutically effective hPCSK9 polypeptide may consist of the amino acid sequence of any one of SEQ ID NO: 36, SEQ ID NO: 37, SEQ ID NO: 42, SEQ ID NO: 43, SEQ ID NO: 47, SEQ ID NO: 56 or combinations thereof.

The isolated or purified therapeutically effective hPCSK9 polypeptide may consist of the combination of the amino acid sequence SEQ ID NO: 36 and SEQ ID NO: 37, SEQ ID NO: 36 and SEQ ID NO: 42 or SEQ ID NO: 36 and SEQ ID NO: 47.

According to another embodiment, there is provided a kit for use for the prevention or the treatment of hypercholesterolemia in a subject in need thereof, the kit comprising:

an isolated or purified therapeutically effective hPCSK9 polypeptide having the amino acid sequence:

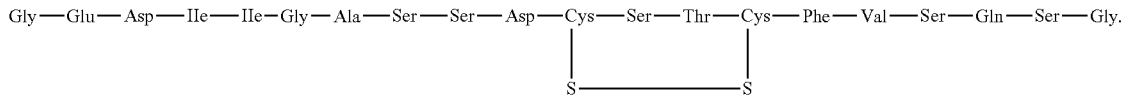

The kit of the present invention may further comprise a HMG-CoA reductase inhibitors (statin).

The HMG-CoA reductase inhibitors (statin) may be for use before, at the same time or after said hPCSK9 polypeptide.

The following terms are defined below.

The term «composition» as used herein is intended to encompass a product comprising the specified ingredients in the specified amounts, as well as any product which results, directly or indirectly, from combination of the specified ingredients in the specified amounts. Such term in relation to pharmaceutical composition or other compositions in general, is intended to encompass a product comprising the active ingredient(s) (i.e. the polypeptides of the present invention) and the inert ingredient(s) (i.e. the pharmaceutically acceptable carriers) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions or other compositions in general of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

The terms "inhibit", "inhibition" or "inhibiting" as used herein in the context of the invention means to slow, hinder, restrain reduce or prevent. For example, "inhibiting growth" of a tumor cell as that term is used herein means to slow, hinder, restrain, reduce or prevent the tumor cell from growing.

The term "administering" as used herein refers to any action that results in exposing or contacting a composition containing a therapeutic IgE antibody specific for a cancer antigen, an antigen present in or around a stroma of a tumor, or a combination thereof, alone or in combination with at least one anti-cancer agent. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells, or by direct intra-tumoral injection of the therapeutic IgE antibody specific for a cancer antigen, an antigen present in or around a stroma of a tumor, or a combination thereof with at least one anti-cancer agent individually or in a mixture.

A "subject" is preferably a human subject but can also be any mammal, including an animal model, in which modulation of an autoimmune reaction is desired. Mammals of interest include, but are not limited to: rodents, e.g. mice, rats; livestock, e.g. pigs, horses, cows, etc., pets, e.g. dogs, cats; and primates. A subject may also be referred to herein as a "patient".

The terms "treatment", "treat" and "treating" encompasses alleviation, cure or prevention of at least one symptom or other aspect of a disorder, disease, illness or other condition (collectively referred to herein as a "condition"), or reduction of severity of the condition, and the like. A composition of the invention need not affect a complete cure, or eradicate every symptom or manifestation of a disease, to constitute a viable therapeutic agent.

As is recognized in the pertinent field, drugs employed as therapeutic agents may reduce the severity of a given disease state, but need not abolish every manifestation of the disease to be regarded as useful therapeutic agents. Beneficial or desired clinical results include, but are not limited to, alleviation of symptoms, diminishment of extent of disease, stabilization (i.e., not worsening) of disease, delay or slowing of disease progression, amelioration or palliation of the disease state, remission (whether partial or total, whether detectable or undetectable) and prevention of relapse or recurrence of disease. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient.

"Treatment" can also mean prolonging survival as compared to expected survival if not receiving treatment. In one embodiment, an indication that a therapeutically effective amount of a composition has been administered to the patient is a sustained improvement over baseline of an indicator that reflects the severity of the particular disorder.

By a "therapeutically effective amount" of a composition of the invention is meant an amount of the composition which confers a therapeutic effect on the treated subject, at a reasonable benefit/risk ratio applicable to any medical treatment. The therapeutic effect is sufficient to "treat" the patient as that term is used herein.

As used herein, the terms "co-administration" or administration "in combination" refers to administering to a subject, at least one isolated or purified therapeutically effective hPCSK9 polypeptide derived from one of the amino acid sequence SEQ ID NO: 54, SEQ ID NO: 55, and SEQ ID NO: 58, and other therapeutic agent(s). The other therapeutic agent(s) and or purified therapeutically effective hPCSK9 polypeptide can be administered at the same time, separately, or sequentially, according to the methods disclosed herein.

Before describing the present invention in detail, a number of terms will be defined. As used herein, the singular forms "a", "an", and "the" include plural referents unless the context clearly dictates otherwise.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
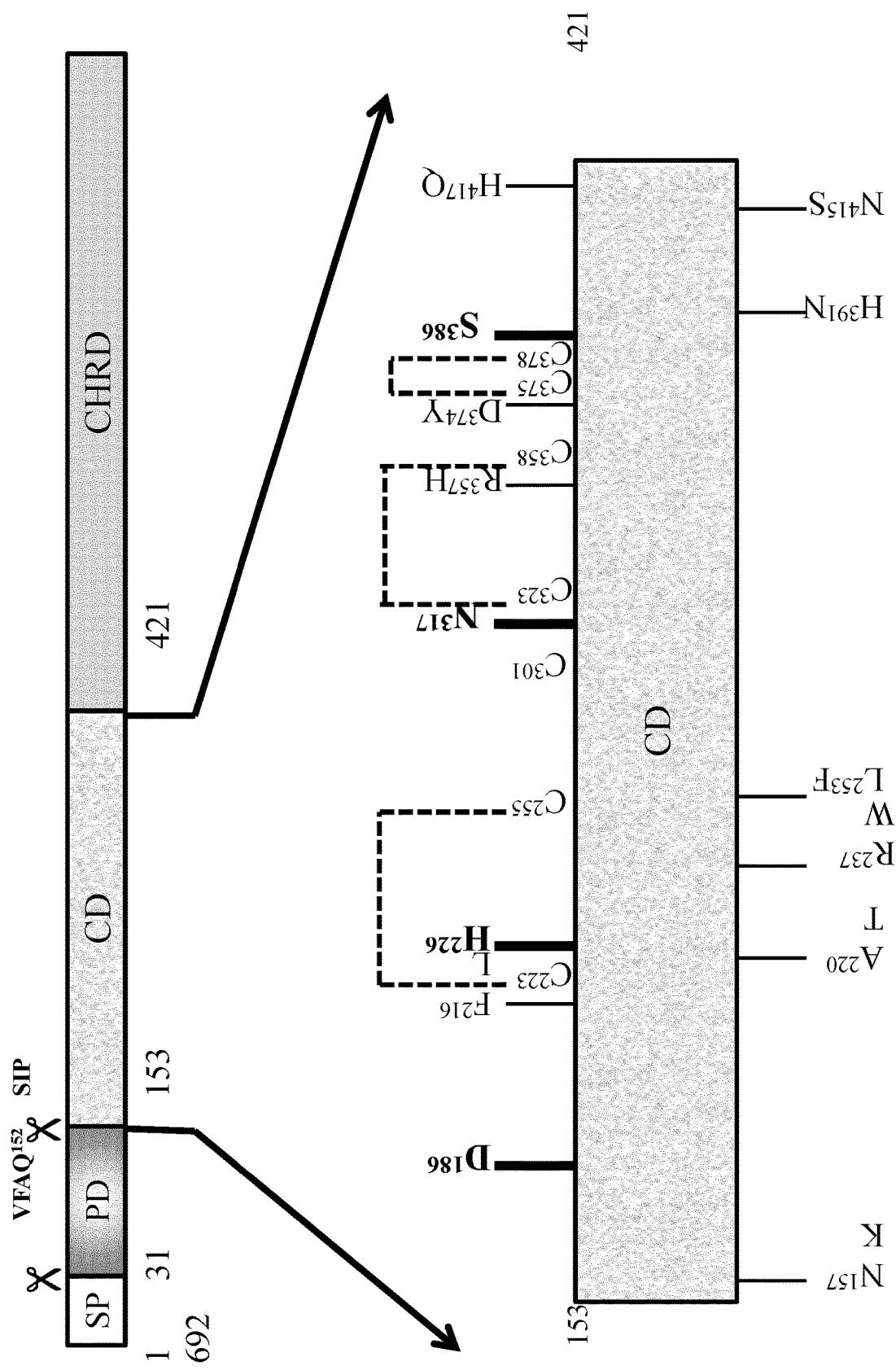
FIG. 1 illustrates a schematic diagram showing the various characteristic domains of human (h) PCSK9 enzyme-cum-protein including its crucial catalytic domain. Upper panel: It shows the complete domain of h-PCSK9; Lower domain: Expanded catalytic domain of hPCSK9. The key catalytic triad residues $D^{186}$, $H^{226}$ and $S^{386}$ along with the oxy-anion $N^{317}$ residues are shown in bold characters and their locations indicated by thick vertical lines. The three known disulphide bonds within the catalytic domain as revealed by its crystal structure are indicated by dotted lines. The lone unpaired $Cys^{301}$ residue is also indicated in the figure. Various gain of function (top side) and the loss of function (bottom side) mutations and their positions are depicted in the figure by regular vertical lines. The abbreviations are as follows: SP=Signal Peptide Domain; PD=Propeptide Domain, CD=Catalytic domain, CHRD=Cysteine-Histidine Rich Domain. The signal peptide and pro-peptide cleavage sites are indicated by scissors.
Figure 2:
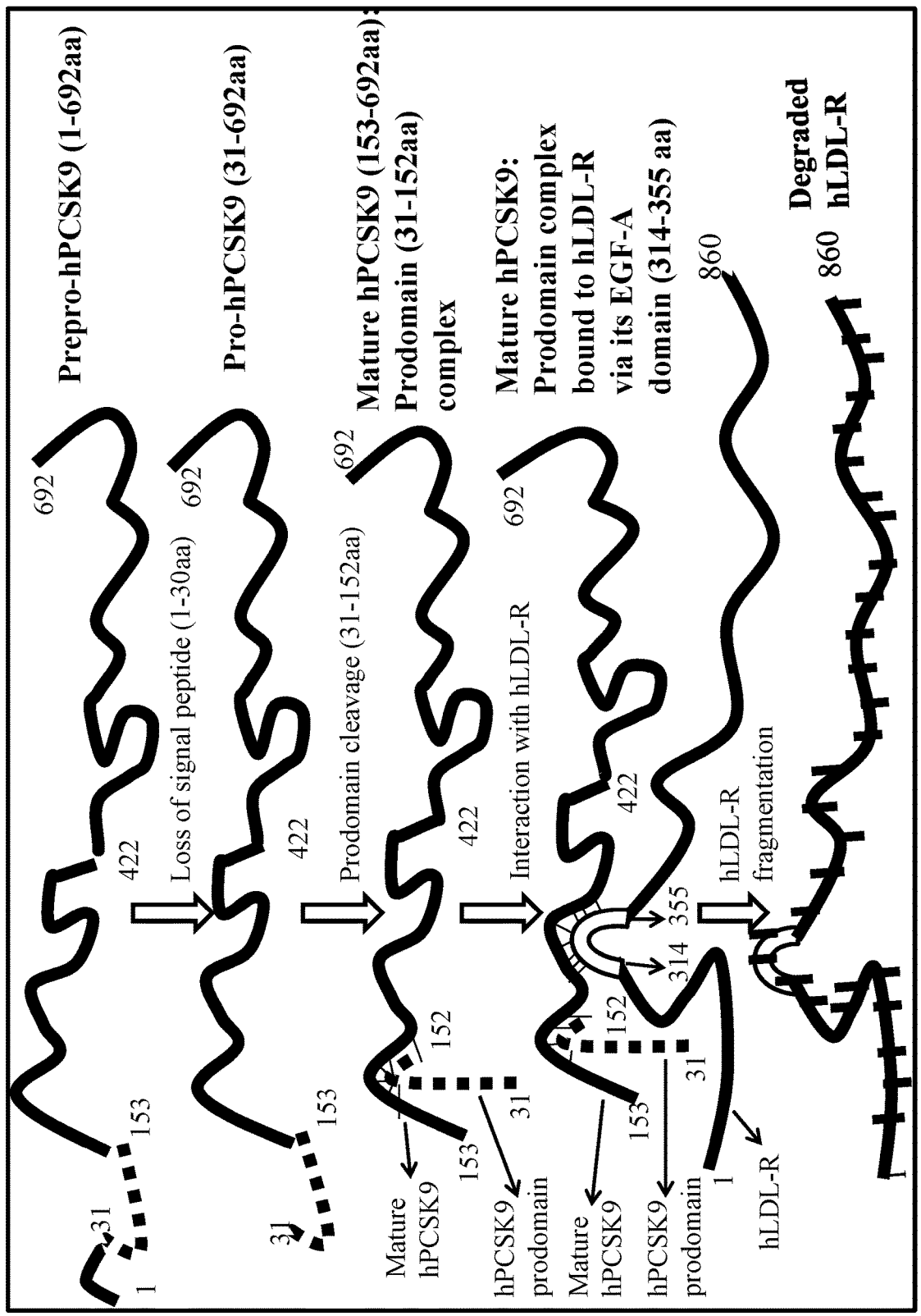
FIG. 2 illustrates a schematic diagram showing the various proposed steps involved in the biosynthesis of functionally active mature hPCSK9 and its subsequent binding with hLDL-R leading to latter's degradation. The figure provides a rational mechanism and pathway for interaction of PCSK9 with LDL-R leading to re-routing of the latter from endosomal to lysosomal pathway for ultimate degradation. The figure demonstrates the initial formation of a strong complex via binding of cleaved prodomain segment (aa31-152) of hPCSK9 with the catalytic segment (shown in thick dark color line; aa153-421) of mature PCSK9 (aa153-692). Subsequently additional binding of this prodomain bound PCSK9 complex with the Epidermal Growth Factor-A (EGF-A) domain (aa314-355) of hLDL-R leading to latter degradation in the lysosome is also depicted in the figure. This binding interaction is most likely mediated via yet unknown region of catalytic domain of PCSK9 as revealed by various studies. (aa=Amino acid).

In embodiments there is disclosed isolated or purified therapeutically effective hPCSK9 polypeptides derived from the amino acid sequence

```
                                    SEQ ID NO: 54)
(CLYSPASAPEVITVGATNAQDQPVTGTLG1TNFGR)
or
                                    SEQ ID NO: 55
(IIGASSDCSTCFVSQSGTSQAAAHV),
or
                                    SEQ ID NO: 58
(CVDLFAPGEDIIGASSDCSTCFVSQSGTSQAAAHVAGIAA).
```

In embodiments, the isolated or purified therapeutically effective hPCSK9 polypeptide of the present invention may consist of the amino acid sequence of any one of SEQ ID NOS: 35 (CLYSPASAPEVITVG), 36 (ASAPEVITVGATNAQ), 37 (VITVGATNAQDQPVT), 38 (ATNAQDQPVTLGTLG) (DQPVTLGTLGTNFGR), 42 (CVDLFAPGEDIIGAS). 43 (APGEDIIGASSDCST), 44 (IIGASSDCSTCFVSQ), 45 (SDCSTCFVSQSGTSQ), 46 (CFVSQSGTSQAAAHV), 47 (SGTSQAAAHVAGIAA) and 56 (GEDIIGASSDCSTCFVSQSG).

According to an embodiment, the isolated or purified therapeutically effective hPCSK9 polypeptide may be a disulphide bridged cyclic peptide. According to another embodiment, the isolated or purified therapeutically effective hPCSK9 polypeptide consists of the amino acid sequence SEQ ID NO:56 and may be a disulphide bridged cyclic peptide. For example, the isolated or purified therapeutically effective hPCSK9 polypeptide may have the amino acid sequence:

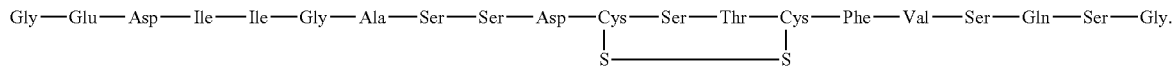

According to another embodiment, there is provided a pharmaceutical composition comprising a therapeutically effective amount of an isolated or purified therapeutically effective hPCSK9 polypeptide of the present invention, or combinations thereof, and a pharmaceutically acceptable carrier.

According to yet another embodiment, there is provided a method of preventing or treating hypercholesterolemia, and/or presumably preventing or treating associated cardiovascular diseases risks, by administering to a subject in need thereof at least one of an isolated or purified therapeutically effective hPCSK9 polypeptide of the present invention, or a pharmaceutical composition of the present invention. In embodiments, the method may further comprise administering a HMG-CoA reductase inhibitors (statin). The HMG-CoA reductase inhibitors (statin) may be for administration before, at the same time or after said hPCSK9 polypeptide. HMG-CoA reductase inhibitors (statin) include but are not limited to Pravastatin, Fluvastatin, Atorvastatin, Pravastatin, Lovastatin, Cerivastatin, Mevastatin, Pitavastatin, Rosuvastatin, Simvastatin.

In another embodiment, there is provided an isolated or purified therapeutically effective hPCSK9 polypeptide derived from one of the amino acid sequence SEQ ID NO: 54, SEQ ID NO: 55, and SEQ ID NO: 58 for preventing or treating hypercholesterolemia. The isolated or purified therapeutically effective hPCSK9 polypeptide may be consisting of the amino acid sequence of any one of SEQ ID NOS: 35 to 39, SEQ ID NOS: 42 to 47, and SEQ ID NO: 56. The isolated or purified therapeutically effective hPCSK9 polypeptide may be consisting of the amino acid sequence of any one of SEQ ID NO: 36, SEQ ID NO: 37, SEQ ID NO: 42, SEQ ID NO: 43, SEQ ID NO: 47, SEQ ID NO: 56 or combinations thereof. The isolated or purified therapeutically effective hPCSK9 polypeptide may be consisting of the combination of the amino acid sequence SEQ ID NO: 36 and SEQ ID NO: 37, SEQ ID NO: 36 and SEQ ID NO: 42 or SEQ ID NO: 36 and SEQ ID NO: 47.

According to another embodiment, the isolated or purified therapeutically effective hPCSK9 polypeptide having the amino acid sequence:

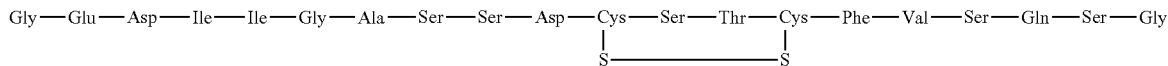

for preventing or treating hypercholesterolemia in a subject in need thereof.

The isolated or purified therapeutically effective hPCSK9 polypeptide of of the present invention may be for use with a HMG-CoA reductase inhibitors (statin). The HMG-CoA reductase inhibitors (statin) is for use before, at the same time or after said hPCSK9 polypeptide. HMG-CoA reductase inhibitors (statin) include but are not limited to Pravastatin, Fluvastatin, Atorvastatin, Pravastatin, Lovastatin, Cerivastatin, Mevastatin, Pitavastatin, Rosuvastatin, Simvastatin.

According to yet another embodiment, there is provided a pharmaceutical composition for use in preventing or treating hypercholesterolemia, comprising a therapeutically effective amount of an isolated or purified therapeutically effective hPCSK9 polypeptide of the present invention, or combinations thereof, and a pharmaceutically acceptable carrier. The pharmaceutical composition of claim 17, further comprising a HMG-CoA reductase inhibitors (statin). The HMG-CoA reductase inhibitors (statin) may be for use before, at the same time or after said hPCSK9 polypeptide. HMG-CoA reductase inhibitors (statin) include but are not limited to Pravastatin, Fluvastatin, Atorvastatin, Pravastatin, Lovastatin, Cerivastatin, Mevastatin, Pitavastatin, Rosuvastatin, Simvastatin.

According to yet another embodiment, there is provided a use of an isolated or purified therapeutically effective hPCSK9 polypeptide derived from one of the amino acid sequence SEQ ID NO: 54, SEQ ID NO: 55, and SEQ ID NO: 58 for preventing or treating hypercholesterolemia. The isolated or purified therapeutically effective hPCSK9 polypeptide is consisting of the amino acid sequence of any one of SEQ ID NOS: 35 to 39, SEQ ID NOS: 42 to 47, and SEQ ID NO: 56. The isolated or purified therapeutically effective hPCSK9 polypeptide is consisting of the amino acid sequence of any one of SEQ ID NO: 36, SEQ ID NO: 37, SEQ ID NO: 42, SEQ ID NO: 43, SEQ ID NO: 47, SEQ ID NO: 56 or combinations thereof. The isolated or purified therapeutically effective hPCSK9 polypeptide is consisting of the combination of the amino acid sequence SEQ ID NO: 36 and SEQ ID NO: 37, SEQ ID NO: 36 and SEQ ID NO: 42 or SEQ ID NO: 36 and SEQ ID NO: 47. The isolated or purified therapeutically effective hPCSK9 polypeptide having the amino acid sequence:

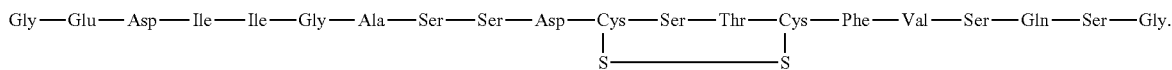

for preventing or treating hypercholesterolemia.

The use may further comprise a HMG-CoA reductase inhibitors (statin). The HMG-CoA reductase inhibitors (statin) may be for use before, at the same time or after said hPCSK9 polypeptide. The HMG-CoA reductase inhibitors (statin) may be for use before, at the same time or after said hPCSK9 polypeptide. HMG-CoA reductase inhibitors (statin) include but are not limited to Pravastatin, Fluvastatin, Atorvastatin, Pravastatin, Lovastatin, Cerivastatin, Mevastatin, Pitavastatin, Rosuvastatin, Simvastatin.

According to yet another embodiment, there is provided a kit for use for the prevention or the treatment of hypercholesterolemia in a subject in need thereof, the kit comprising:

an isolated or purified therapeutically effective hPCSK9 polypeptide derived from one of the amino acid sequence SEQ ID NO: 54, SEQ ID NO: 55, and SEQ ID NO: 58; and instructions on how to use the kit.

The the isolated or purified therapeutically effective hPCSK9 polypeptide is consisting of the amino acid sequence of any one of SEQ ID NOS: 35 to 39, SEQ ID NOS: 42 to 47, and SEQ ID NO: 56. The isolated or purified therapeutically effective hPCSK9 polypeptide is consisting of the amino acid sequence of any one of SEQ ID NO: 36, SEQ ID NO: 37, SEQ ID NO: 42, SEQ ID NO: 43, SEQ ID NO: 47, SEQ ID NO: 56 or combinations thereof. The isolated or purified therapeutically effective hPCSK9 polypeptide is consisting of the combination of the amino acid sequence SEQ ID NO: 36 and SEQ ID NO: 37, SEQ ID NO: 36 and SEQ ID NO: 42 or SEQ ID NO: 36 and SEQ ID NO: 47. The isolated or purified therapeutically effective hPCSK9 polypeptide may have the amino acid sequence:

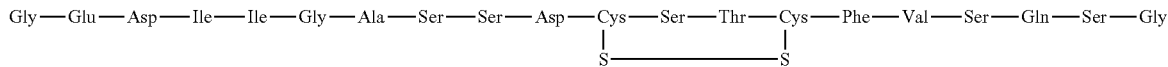

The kit may further comprise a HMG-CoA reductase inhibitors (statin). The HMG-CoA reductase inhibitors (statin) is for use before, at the same time or after said hPCSK9 polypeptide. The HMG-CoA reductase inhibitors (statin) may be for use before, at the same time or after said hPCSK9 polypeptide. HMG-CoA reductase inhibitors (statin) include but are not limited to Pravastatin, Fluvastatin, Atorvastatin, Pravastatin, Lovastatin, Cerivastatin, Mevastatin, Pitavastatin, Rosuvastatin, Simvastatin.

Overall data presented herein indicates that the disulphide bridge containing Loop3 peptide from the catalytic domain of hPCSK9 (connecting the two Cys residues indicated in bold underlined character) defined by the sequence hPCSK9$^{365-384}$ ($^{365}$GEDIIGASSD[C̲S̲T̲C̲]FVSQSG$^{384}$) (SEQ ID NO: 56) is an effective peptide with LDL-R promoting activity when added exogenously to the culture medium of growing HepG2 and HuH7 cells. Other effective peptides include peptides derived from SEQ ID NO: 54 (CLYSPASAPEVITVGATNAQDQPVTGTLG1TNFGR)

or SEQ ID NO: 55 (IIGASSDCSTCFVSQS-GTSQAAAHV), such as SEQ ID NOS: 35 (CLYSPASAPE-VITVG), SEQ ID NO: 36 (ASAPEVITVGATNAQ), SEQ ID NO: 37 (VITVGATNAQDQPVT), SEQ ID NO: 38 (ATNAQDQPVTLGTLG), SEQ ID NO: 39 (DQPVTL-GTLGTNFGR), SEQ ID NO: 42 (CVDLFAPGEDIIGAS), SEQ ID NO: 43 (APGEDIIGASSDCST), SEQ ID NO: 44 (IIGASSDCSTCFVSQ), SEQ ID NO: 45 (SDC-STCFVSQSGTSQ), SEQ ID NO: 46 (CFVSQS-GTSQAAAHV) and SEQ ID NO: 47 (SGTSQAAAHVA-GIAA). The S—S bond between $Cys^{375}$ and $Cys^{378}$ (shown as bold underlined) in the SEQ ID NO: 56 peptide is believed to be critical for this activity, suggesting its role in providing a better binding opportunity with the EGF-A domain of LDL-R. Interestingly this peptide also contains the site for the most potent gain of function mutation, namely $D^{374}$ (shown above in bold italic) to Y. Mimicking this mutation in the peptide (substitution of $D^{374}$ by Y, i.e. $^{365}$GEDIIGASSY[CSTC]FVSQSG$^{384}$, SEQ ID NO: 57) may enhance its bioactivity and promote LDL-R level even more. The peptides of the present invention may represent the first generation of small compound agent which can be further exploited to enhance its LDL-R promoting activity and prevent or treat hypercholesterolemia, and/or presumably preventing or treating associated cardiovascular diseases risks.

The present invention will be more readily understood by referring to the following examples which are given to illustrate the invention rather than to limit its scope.

Example 1

Experimental Description

Materials

All Fmoc amino terminal protected amino acids (L-configuration) with additional side chain protection as needed, peptide coupling reagents namely HBTU, PAL-PEG-PS resin for peptide synthesis, organic solvents such as Acetontrile (CAN, HPLC grade) and Dimethyl formamide (DMF, analytical grade) were obtained from Bachem Inc (Torrance, Ca, USA), Calbiochem Novabiochem Inc, (San Diego, Ca, USA), Neosystems Inc, (Strasbourg, France) and PE-Biosystems (Foster City, Ca, USA). TFA and all reagents such as phenol, TIS and EDT constituting Reagent B [Palmer Smith H, Basak A. Regulatory Effects of Peptides From the Pro and Catalytic domains of Proprotein Convertase Subtilisin/Kexin 9 (PCSK9) on LDL-R. *Curr Med Chem,* 17(20):2168-2182, 2010] for peptide deprotection and its cleavage from resin were purchased from Sigma-Aldrich Chemical (Milwaukee, USA). TCEP [Tris (2-carboxy ethyl) phosphine], Iodoacetamide as well as all other coupling agents and organic solvents were bought from Sigma-Aldrich, VWR or Fisher companies.

Matrix Assisted Laser Desorption (MALDI) and Surface Enhanced Laser Desorption Ionization (SELDI) time of flight (tof) mass spectra (MS) were recorded using Voyageur (PE-Biosystems, Framingham, Ma, USA) and Ciphergen Protein Chips (Fremont, Ca, USA) respectively. The corresponding mass spectra plates, re-usable gold plates for SELDI and stainless plates for MALDI were purchased from the respective companies. α-Cyano 4-hydroxy cinnamic acid (CHCA), 2,5-Di-hydroxy benzoic acid (DHB) and Sinapic (Sigma-Aldrich Chemical) were used as energy absorbing matrices for low and high molecular weight compounds respectively. Reagents for western blot and SDS-PAGE analyses were purchased from Bio-rad Labs (Hercules, Ca, USA). All chemi-luminescence reagents (Perkin Elmer LAS Inc, Shelton, Conn., USA) were used for detection of immuno-reactive bands. Images were captured using Kodak X-OMAT Blue autoradiography film (PerkinElmer LAS Inc., Waltham, Ma, USA).

Antibodies

Polyclonal antibodies against hLDL-R (#CY-M1033), hPCSK9 (#AF2148) and Transferrin receptor (#13-6800) were purchased from R&D Systems, Circulex and Invitrogen companies respectively. Aβ-actin-HRP (Horse Radish Peroxidase) (#ab49900) and αFLAG-HRP (#1238) primary antibodies were both bought from ABCAM Company. Goat-HRP (#ab6741) and α mouse-HRP (#172-1011) secondary antibodies were obtained from ABCAM and Bio-rad company respectively.

Peptide Synthesis hPCSK9 Catalytic Domain Derived Peptides.

All 51 peptides were derived from hPCSK9 catalytic domain which is implicated in binding with EGF-A-domain of LDL-R. Each of these peptides is comprised of 15 aa except for the last one P51 which is 18 aa long (listed in Table 1). They were all synthesized on an automated solid-phase peptide synthesizer instrument (Intavis, Multipep model, Germany) using Fmoc (Fluorenyl methoxy carbonyl) mediated chemistry and HBTU [N,N,N',N'-Tetramethyl-O-(1H-benzotriazol-1-yl) uronium hexafluorophosphate], HOBT (1-Hydroxy benzotriazole) in presence of DIEA (N, N'-diisopropyl ethyl amine) as coupling reagent [Palmer Smith H, Basak A. Regulatory Effects of Peptides From the Pro and Catalytic domains of Proprotein Convertase Subtilisin/Kexin 9 (PCSK9) on LDL-R. *Curr Med Chem,* 17(20):2168-2182, 2010]. The following amino acid side chain protecting groups were used: Pbf (2,2,4,6,7-pentamethyldihydrobenzofuran-5-sulfonyl) for Arg; tBu (tertiary butyl) for Ser, Thr, Tyr, Asp and Glu residues; Trityl (triphenyl methyl) for Cys, His, Gln and Asn and Boc (t-butyloxy carbonyl) for Lys. The synthesis started from carboxy (C—) to amino terminus (N—) end on an unloaded Fmoc-protected tentagel [a PAL-PEG {poly amino linker poly ethylene glycol} cross linked to PS (polystyrene)] resin. Following the end of synthesis, peptides were cleaved off from the resin and fully deprotected at the same time by 3 h treatment with Reagent B consisting of 90% TFA (Trifluoroacetic acid), 2.5% phenol, 5% water and 2.5% TIS (Tri-isopropyl silane) [Palmer Smith H, Basak A. Regulatory Effects of Peptides From the Pro and Catalytic domains of Proprotein Convertase Subtilisin/Kexin 9 (PCSK9) on LDL-R. *Curr Med Chem,* 17(20):2168-2182, 2010, Mishra, P et. al. In vitro regulatory effects of epidydimal serpin CRES on protease activity of Proprotein Convertase 4 (PC4). *Current Molecular Medicine.* 12, 1050-1067, 2012] for 3 h at ambient temperature. The crude peptides thus obtained were purified by RP-HPLC as described later and fully characterized by MALDI—(Matrix Assisted Laser Desorption Ionization) (Voyageur, Applied Biosystems) or SELDI (Surface Enhanced Laser Desorption Ionization)-tof (time of flight) Mass Spectrometer (MS) (Protein chips, Ciphergen, Fremont, Calif., USA) using CHCA, DHB or SPA as an energy absorbing matrix.

TABLE 1

List of 51 (P1-P51) peptides (15 aa long with 10aa overlapping sequence) derived from hPCSK9 catalytic domain and their molecular weights (MWs).

| Name | Amino acid sequence | MW | Calc MW Peptide: FI-EGF-A 1:1 adduct |
|---|---|---|---|
| P1 | SIPWNLERITPPRYR | 1898.0 | 6860.5 |
| P2 | LERITPPRYRADEYQ | 1907.0 | 6895.5 |
| P3 | PPRYRADEYQPPDGG | 1717.8 | 6680.3 |
| P4 | ADEYQPPDGGSLVEV | 1575.7 | 6538.2 |
| P5 | PPDGGSLVEVYLLDT | 1574.8 | 6537.3 |
| P6 | SLVEVYLLDTSIQSD | 1681.9 | 6644.4 |
| P7 | YLLDTSIQSDHREIE | 1818.9 | 6781.4 |
| P8 | SIQSDHREIEGRVMV | 1755.9 | 6718.4 |
| P9 | HREIEGRVMVTDFEN | 1831.9 | 6794.4 |
| P10 | GRVMVTDFENVPEED | 1736.8 | 6699.3 |
| P11 | TDFENVPEEDGTRFH | 1792.8 | 6755.3 |
| P12 | VPEEDGTRFHRQASK | 1756.9 | 6719.4 |
| P13 | GTRFHRQASKCDS_H_G | 1686.8 | 6649.3 |
| P14 | RQASKCDS_H_GTHLAG | 1567.8 | 6530.3 |
| P15 | CDS_H_GTHLAGVVSGR | 1495.7 | 6458.2 |
| P16 | THLAGVVSGRDAGVA | 1409.8 | 6372.3 |
| P17 | VVSGRDAGVAKGASM | 1404.7 | 6367.2 |
| P18 | DAGVAKGASMRSLRV | 1630.9 | 6593.4 |
| P19 | KGASMRSLRVLNCQG | 1619.9 | 6582.6 |
| P20 | RSLRVLNCQGKGTVS | 1617.9 | 6580.4 |
| P21 | LNCQGKGTVSGTLI G | 1447.8 | 6410.3 |
| P22 | KGTVSGTLIGLEFIR | 1590.9 | 6553.4 |
| P23 | GTLIGLEFIRKSQLV | 1674.0 | 6636.5 |
| P24 | LEFIRKSQLVQPVGP | 1711.0 | 6673.5 |
| P25 | KSQLVQPVGPLVVLL | 1590.0 | 6552.5 |
| P26 | QPVGPLVVLLPLAGG | 1429.9 | 6392.4 |
| P27 | LVVLLPLAGGYSRVL | 1570.0 | 6532.5 |
| P28 | PLAGGYSRVLNAA*C*Q | 1519.8 | 6482.3 |
| P29 | YSRVLNAA*C*QRLARA | 1691.9 | 6654.4 |
| P30 | NAA*C*QRLARAGVVLV | 1540.9 | 6503.4 |
| P31 | RLARAGVVLVTAAGN | 1467.9 | 6430.4 |
| P32 | GVVLVTAAG_N_FRDDA | 1504.8 | 6467.3 |
| P33 | TAAG_N_FRDDACLYSP | 1600.7 | 6563.2 |
| P34 | FRDDACLYSPASAPE | 1641.7 | 6604.2 |
| P35 | CLYSPASAPEVITVG | 1506.8 | 6469.3 |
| P36 | ASAPEVITVGATNAQ | 1428.7 | 6391.2 |
| P37 | VITVGATNAQDQPVT | 1513.8 | 6476.3 |
| P38 | ATNAQDQPVTLGTLG | 1485.8 | 6448.1 |
| P39 | DQPVTLGTLGTNFGR | 1575.8 | 6538.3 |
| P40 | LGTLGTNFGRCVDLF | 1612.8 | 6575.3 |
| P41 | TNFGRCVDLFAPGED | 1640.7 | 6603.2 |
| P42 | CVDLFAPGEDIIGAS | 1506.7 | 6469.2 |
| P43 | APGEDIIGASSDCST | 1422.6 | 6385.1 |
| P44 | IIGASSDCSTCFVSQ | 1517.7 | 6480.2 |
| P45 | SDCSTCFVSQSGT_S_Q | 1536.6 | 6499.1 |
| P46 | CFVSQSGT_S_QAAAHV | 1492.7 | 6455.2 |
| P47 | SGT_S_QAAAHVAGIAA | 1311.7 | 6274.2 |
| P48 | AAAHVAGIAAMMLSA | 1384.7 | 6347.2 |
| P49 | AGIAAMMLSAEPELT | 1504.7 | 6467.2 |
| P50 | MMLSAEPELTLAELR | 1703.9 | 6666.4 |
| P51 | EPELTLAELRQRLIHFSA | 2123.2 | 7085.7 |

Table 1 lists of 51 (P1-P51) peptides (15 aa long with 10 aa overlapping sequence) (SEQ ID NO: 1 to 51) derived from hPCSK9 catalytic domain and their molecular weights (MWs). The calculated (Calc) MWs of 1:1 complex between peptide and FI-EGF-A (MW=4962.5 Da) which range from 6274.2 (for P47) and 7085.7 Da (for P51) were also shown. The catalytic triads $D^{186}$, $H^{226}$ and $S^{386}$ and the oxyanion $N^{317}$ residue were shown with underline whereas the crucial $D^{374}$ whose natural mutation to Y leads to most potent gain of function is depicted in bold. The second most potent gain of function mutation $R^{357}$ to H is also shown in bold. The single presumed unpaired Cys residue at position 301 is indicated in bold italics character.

FI/Bio-EGF-A peptide (Ia and Ib).

Figure 3:
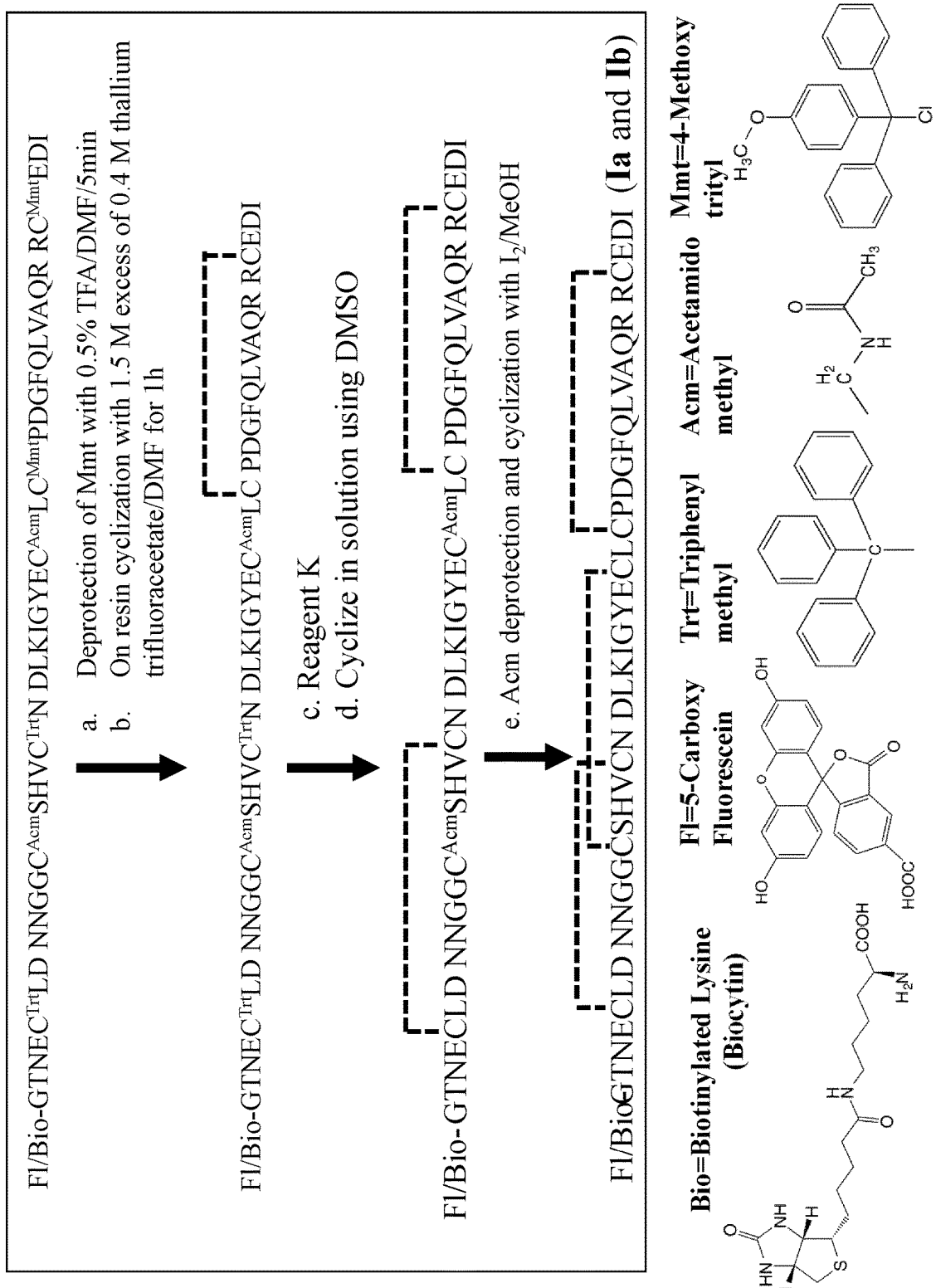
FIG. 3 illustrates a chemical scheme for the synthesis of Fluorescein (Fl) (Ia) and Biotin (Bio) (Ib) labeled EGF-A peptide (residue aa314-355 of hLDL-R). The dotted lines indicate the S—S bond connectivity of 6 Cys residues present in the sequence. In all there are three disulphide bonds as indicated. The various reagents and coupling agents used are shown in each step. Three pairs of Cys side chain protecting groups namely Mmt, Trt and ACM were used in the synthesis in order to ensure the correct S—S bond formations as present endogenously in the EGF-A domain of hLDL-R protein. The first S—S bond formation was achieved while the protected peptide is still bound on the resin by deprotecting the Mmt group under mild condition. All side chain protecting groups except the two Cys-ACM groups were then fully deprotected by two 3 hour treatments with Reagent K (82.5% TFA+5% Phenol+5% Water+5% Thioanisole+2.5% EDT). This is then further cyclized by treatment with DMSO (N—N' Dimethyl sulphoxide) for 3 hours. The double S—S bridges containing peptide thus obtained was then lyophilized and two protecting ACM groups were then removed by treatment with iodine in methyl alcohol (MeOH) which also led to the formation of third S—S bond as indicated in the figure. These led to the formation of FI-EGF-A which was labeled either with 5-Carboxy Fluorescein or Biotin.

The synthesis of fluorescein labeled EGF-A peptide (FI-EGF-A) was carried out by using unloaded Fmoc-protected tentagel PS resin and Fmoc-mediated solid phase peptide chemistry with minor modification of triple couplings in each cycle instead of usual double coupling as described previously [Mishra, P et al. In vitro regulatory effects of epidydimal serpin CRES on protease activity of Proprotein Convertase 4 (PC4). *Current Molecular Medicine*. 12, 1050-1067, 2012]. Three pairs of Cys protecting groups namely the highly acid labile Mmt group, ACM and Trt were used as indicated in FIG. 3 during the synthesis. This will allow S—S bridge connections between right Cys residues (namely $Cys^1$-$Cys^3$, $Cys^2$-$Cys^4$ and $Cys^5$-$Cys^6$, numbered from N-terminal end) as present physiologically in the EGF-A domain of hLDL-R protein. Following the completion of the peptide assembly, the final attachment (via the peptide's free amino terminal) of fluorescein group using activated 5-Carboxy fluorescein or Biotin moiety was accomplished by HBTU/HOBT activating agent. The fully protected labeled peptide still bound on the resin was then treated with 0.5% TFA/DMF for 5 min (2 times) to remove specifically the acid labile Mmt protecting group on $Cys^6$ and $Cys^5$. On resin cyclization via S—S bridge formation between these two free Cys residues were performed by treatment with 1.5M excess of 0.4 M thallium trifluoroacetate/DMF for 1 h following the protocol described before [Angeletti R H, et al. Formation of a Disulfide Bond in an Octreotide-Like Peptide: A Multicenter Study, *Techniques in Protein Chemistry VII*, Academic Press, Inc. 1996.]. The resin is next treated with Reagent B for 3 h to remove all the protecting groups except the two ACM groups on $Cys^2$ and $Cys^4$ and cleave the peptide from the resin. The recovered material following lyophilisation was treated with DMSO to induce S—S bridge cyclization between the two free $Cys^1$ and $Cys^3$ residues. Next the two ACM protecting groups were removed from $Cys^2$ and $Cys^4$ by treatment with 12 in MeOH and cyclised at the same time to furnish Fl/Bio-EGF-A peptide (Ia and Ib). The peptides were purified by RP-HPLC and fully characterized by mass spectrometry Fl-Bio-Ahx-Lys-Methyl Ester (IIId).

Figure 4:
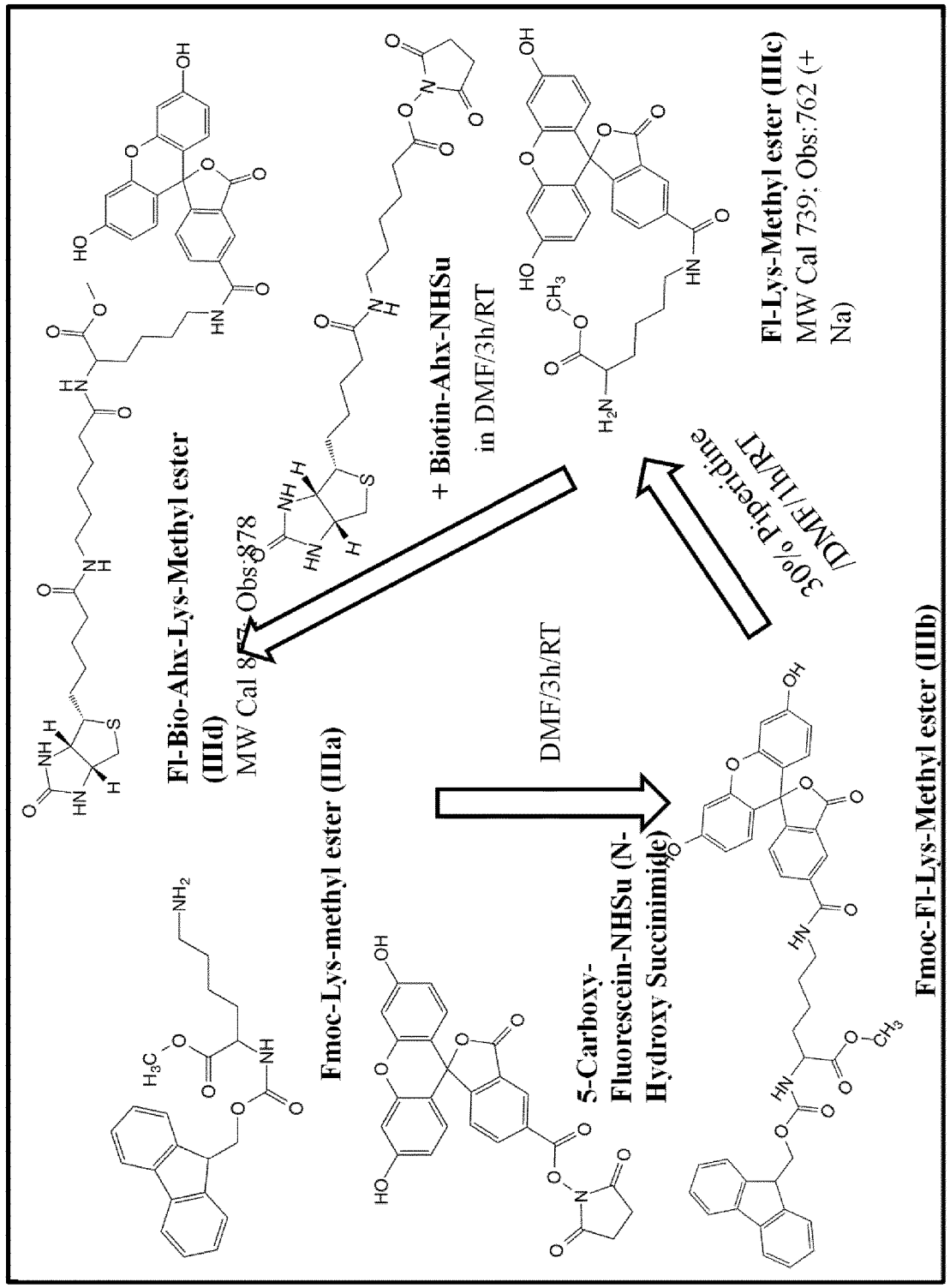
FIG. 4 illustrates a scheme showing various steps involved in the chemical synthesis of FI-Bio-Ahx-Lys-Methyl ester (III)—model compound used for fluorescence study. The synthesis was accomplished by first coupling Fmoc-Lys-methyl ester (IIIa) with 5-Carboxy Fluorescein N-Hydroxy succinimide followed by deprotection of Fmoc group with 20% Piperidene/DMF. The product thus obtained was then coupled with Biotin-Ahx NHSu. Ahx=Amino hexanoic acid (serves as a linker) for the biotin derivative.

Fluorescent biotinylated lysine methyl ester [Fl-Bio-Ahx-Lys-Methyl ester] (IIId), used as a model compound in the current study was synthesized by using the steps and reagents shown in FIG. 4. Here Ahx (epsilon amino hexanoic acid) serves as a linker. Typically Fmoc-Lysine Methyl ester (Bechem Inc) (1 mmol) was first labeled with 5-Carboxy Fluorescein via its side chain free amino group by reacting with 5-carboxy fluorescein-NHSu (N-hydroxy succinimide). The labeled product (IIIb) was then treated with 30% piperidine in DMF to remove the protecting Fmoc group. The resulting free amino derivative (IIIc) thus obtained was finally reacted with Biotin-Ahx-NHSu leading to the formation of Fl-Bio-Ahx-Lys-Methyl ester (IIId), which was purified by silica gel column chromatography and fully characterized by mass spectrometry (Calculated MW=877, observed MW=878 (M++H).

Peptide Purification by RP-HPLC.

All crude peptides except Fl-Bio-Ahx-Lysine methyl ester (IIIb) were purified by Reverse Phase High Performance Layer Chromatography (RP-HPLC) using $C_{18}$ Silica gel analytical column (Varian, 1×25 cm size). During RP-HPLC purification, proteins were separated using a linear gradient of Solvent B from 10% to 90% in Solvent A [Solvent B=0.1% TFA in ACN and Solvent A=0.1% TFA in water]. Fractions were collected and analyzed as the elution was monitored on-line by UV detector with wavelength fixed at 230 nm. Peaks were collected, lyophilized and subjected to mass spectrometry for their identifications.

Cell Culture

The human hepatic HepG2 cells were maintained at 37° C. with 5% $CO_2$ in Dulbecco's modified Eagle's medium (DMEM) (Wisent #319-005-CL) supplemented with 10% fetal bovine serum (Wisent #080-350) as well as penicillin and streptomycin (Wisent #450-201-EL). The number passages of cell lines used were 6-8 times until they are at least 80% confluent as determined by microscope. For each culture experiment, nearly 1 million cells were seeded in a petri dish. Each synthetic peptide was dissolved in DMSO solvent at 1 mM concentration and stored at −20° C. before use. The peptide treatments (final concentration 10 µM unless otherwise specified) were carried out by adding the solution in the fresh culture medium. The cells were grown for additional for 16 h. The medium was removed and the cells were washed twice with PBS buffer. The residual cells were finally collected in PBS buffer using cell scrapers. It was the centrifuged and the cell pellet thus obtained was lysed in modified RIPA buffer (50 mM Tris-HCl (pH 7.4), 150 mM NaCl, 1 mM EDTA, 1% Triton X-100, 0.5% sodium deoxycholate, 0.1% SDS, 1% Nonidet P-40) containing protease and phosphatase inhibitors (Sigma Aldrich #P8340 and #P5726). All culture samples including whole cell lysate (WCL) were analysed for their protein contents using Pierce BCA (Bicinchoninic acid) reagent method or Bradford assay (Bio-Rad #500-0205) as described later.

Protein Assay

Total protein content in a sample was measured by using Bradford's optical density or BCA methods. Each sample was mixed with Coomassie reagent (Bio-rad) and optical density (OD) value was measured using Multiskan® Spectrum (Thermo) plate following the protocol of the manufacturer.

Western Blot Analysis and SDS-PAGE

In general 20 µg of WCLs derived from various peptide treated HepG2 cell experiments was resolved by conventional 12% SDS-PAGE (Laemmli, 1970 #2). Resolved samples were then transferred to polyvinylidene fluoride (Bio-Rad #162-0177) and probed for LDL-R (R&D Systems #AF2148), hPCSK9 (Circulex #CY-M1033), Transferrin Recepter (TR) (Invitrogen #13-6800), αβ-actin-HRP (Horse Radish Peroxidase) (abcam #ab49900) and αFLAG-HRP (abcam #1238) primary antibodies and detected with α goat-HRP (abcam #ab6741) or a mouse-HRP (Bio-Rad #172-1011) secondary antibodies and visualized on a Bio-Rad versa dock imaging system using Clarity ECL Western Substrate (Bio-Rad #170-5060). All cell culture and western blot experiments have been repeated three times and the average results and data were shown.

Recombinant hPCSK9 WT and D/Y

Recombinant PCSK9 wild type (WT) as well as $D^{374}/Y$ mutant both containing a C-terminal FLAG tag (Sequence: DYKDDDDK) was expressed and purified. The protein was characterized by SDS-gel electrophoresis, western blot and mass spectral analyses.

In Vitro Binding Assays

Binding assays of various PCSK9 peptides were carried out by incubating 15 µg of each peptide (~0.008 mM) with 20 µg of Fl-EGF-A in a final volume of 20 µl of 25 mM HEPES (pH 7.4), 150 mM NaCl, 2 mM $CaCl_2$ for 2 h at 37° C. Similar study was also performed using recPCSK9 wild type as well as D/Y variants against Fl-EGF-A. Each sample along with the control without any added peptide was assessed for any binding between Fl-EGF-A and peptide using fluorescence study, Mass spectrometry and Native gel studies Fluorescence Study:

The fluorescence intensity of Fl-EGF-A peptide solution in water (typically 5 µl of 0.5 mM concentration) was measured in the absence and presence of aqueous solution (10 µl, 0.5 mM concentration) of each hPCSK9 catalytic peptide (P1-P51) solution at $\lambda_{ex}$ and $\lambda_{em}$ fixed at 490 and 514 nm respectively following incubation for 1 h at 37° C. with shaking (70 rpm). The experiment was conducted in a 96-microtitre well plate (black color, 50 µl capacity) using fluorescence spectrophotometer (Molecular Devices Co, USA).

SELDI-tof-Mass Spectrometry:

SELDI-Tof mass spectrum was performed on gold plate chips with 2 µl of sample and 2 µl of SPA matrix as described in Palmer et al. and Mishra et al. Each spectrum of peptide sample was calibrated against hInsulin (MW 5,807 Da) both as internal and external standards. For mass spectrum of samples containing rec-hPCSK9, the calibration was performed against BSA (MW 66,120 Da) and Carbonic Anhydrase (MW 16,998 Da).

Native Gel Electrophoresis:

Native gel electrophoresis was performed on each incubated sample under SDS free condition in Tris-Glycine gel. Typically 5 µl of each peptide sample was pre-incubated with 20 µl of buffer at room temperature under mild condition and loaded onto Tris-Tricine gel (1 mm thick) along with appropriate standards. The bands were revealed upon staining with Coomassie blue dye.

Fluorescence Gel Electrophoresis:

This is performed on the samples (typically 5 µl) containing Fl-EGFA+rec-PCSK9 WT or its D/Y variants as well as the corresponding control consisting of Fl-EGF-A alone in buffer. The bands were resolved on Native-PAGE as indicated before and revealed under UV light in the dark. A mixture of fluorescent standard markers was also run in parallel.

MTT Assay

MTT assays were carried out in 96 well plates in triplicate according to the manufacturer's protocol (Biotium #30006). These provide a measurement of cell viability. This is a highly sensitive method which measures cell proliferation based on the reduction of 3 [4,5-Dimethylazol-2-yl] 2,5 diphenyl—Tetrazolium Bromide Tetrazolium salt (MTT).

Statistical Analysis

Unless otherwise indicated, results were compared using Student's t test. A p value of less than 0.05 was considered significant. Each experiment was performed in triplicates and the data were used for statistical purposes.

Example 2

Peptide Design, Purification and Characterization hPCSK9 Catalytic Peptides (P1-P51)

The binding of hPCSK9, a secreted soluble protein with the membrane bound receptor hLDL-R has been the subject of intense investigation in recent years. Studies now revealed that hPCSK9 binds to hLDL-R via the extracellular 42 aa long EGF-A domain of the latter that also possesses a strong $Ca^{+2}$ binding site. Interestingly the precise binding segment of the other partner molecule namely hPCSK9 has not been fully ascertained although all indications point to its catalytic domain (aa153-421). This was finally confirmed by the crystal structures of recombinant hPCSK9 complex with LDL-R or synthetic EGF-A peptide. However which specific peptide sequence/s of PCSK9 catalytic segment is associated with this binding remained unclear.

In an effort to define this a series of peptides (P1-P51; SEQ ID NOS:1 to 51) of 15 mer length (except the 18-mer last peptide P51) has been designed that encompass the entire catalytic domain of hPCSK9. Moreover each of these peptides shares 10 aa overlapping sequences with the immediate preceeding one. The list of these peptides with their amino acid sequences and locations are shown in Table-1. The four important catalytic residues $\underline{D}^{186}$, $\underline{H}^{226}$, $\underline{N}^{317}$ and $\underline{S}^{386}$ as well as the two most potent gain of function mutations ($\underline{D}^{374}$/Y (and $\underline{R}^{357}$/H) in these peptides were highlighted. In addition, the seven Cys residues, 6 of which are inter-linked via S—S bridges were also highlighted in underlined regular character. Following purification by RP-HPLC, these peptides exhibited in their mass spectra peaks at m/z values consistent with the calculated value (Table-1).

Table-1 also shows the calculated molecular weights of 1:1 complex of these peptides with synthetic Fl-EGF-A (see later).

Fl-EGF-A (Ia) and Bio-EGF-A (Ib)

Figure 5:
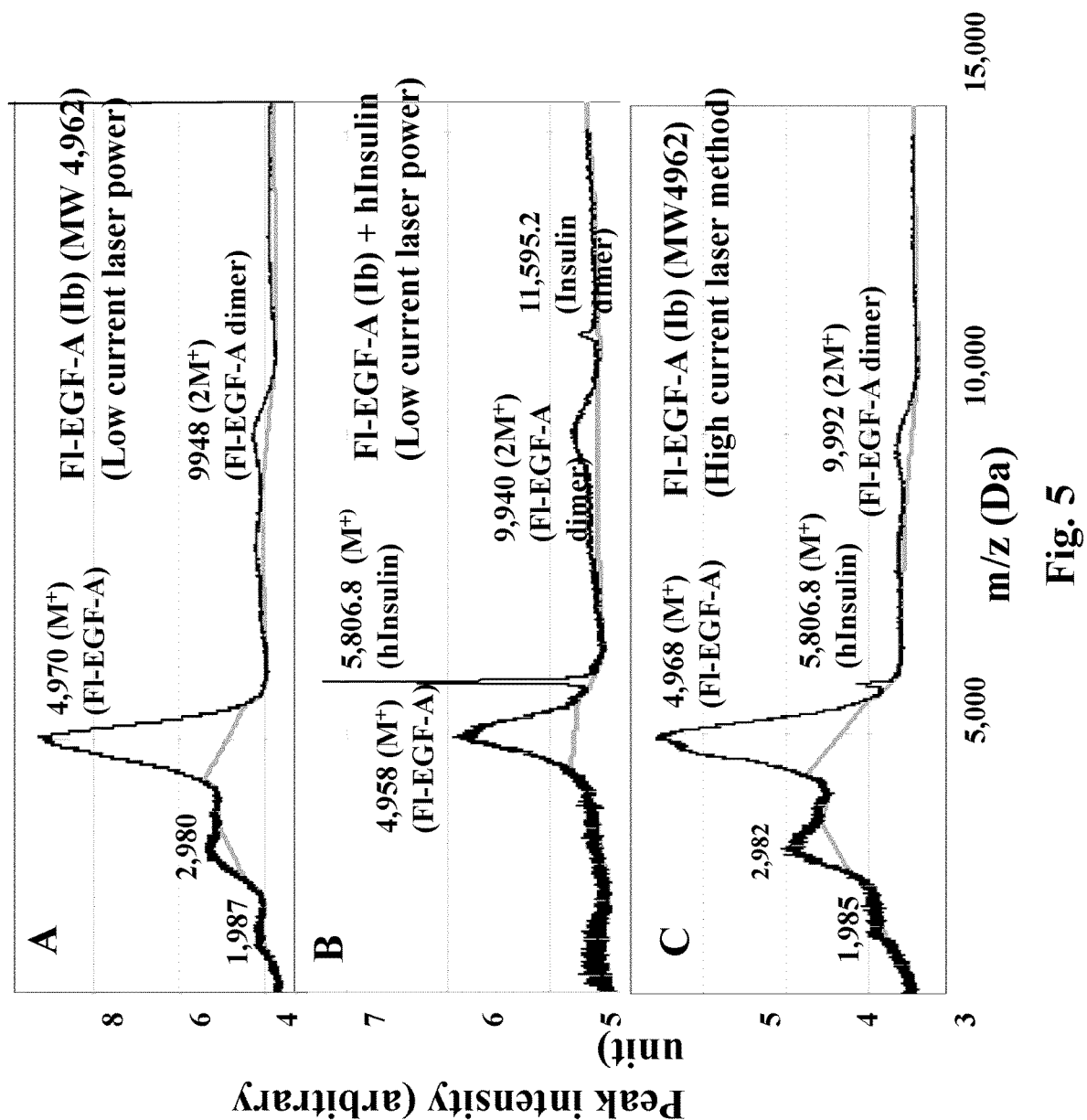
FIG. 5 illustrates SELDI-Tof mass spectrum of purified FI-EGF-A peptide. (Ia): Mass spectrum using Low (A, B) and High current (C) laser method conditions. The mass spectra were calibrated against standard h-Insulin added as internal standard (MW 5,807 Da) and conducted using sinapic acid (SPA) as matrix. Calculated MW of FI-EGF-A=4,962.45 Da (Dalton).

This peptide is designed from the EGF-A domain of hLDL-R which comprises the segment (aa314-355). A 5-Carboxy Fluorescein moiety is attached to the free amino terminus of this peptide while it is still resin bound with all amino acid side chain functions protected. The fluorescein labeled free fully cyclized peptide (FIG. 3) (see above for details) is then purified by RP-HPLC and characterized by SELDI-tof mass spectrum (FIG. 5) which showed a peak at m/z~4,958. This is consistent with the calculated value of m/z 4,962. The presence of three S—S bridges in the peptide was confirmed by alkylation and reductive alkylation experiments. As revealed by mass spectra (not shown), Fl-EGF-A remains unreacted upon treatment with iodoacetamide.

Figure 6:
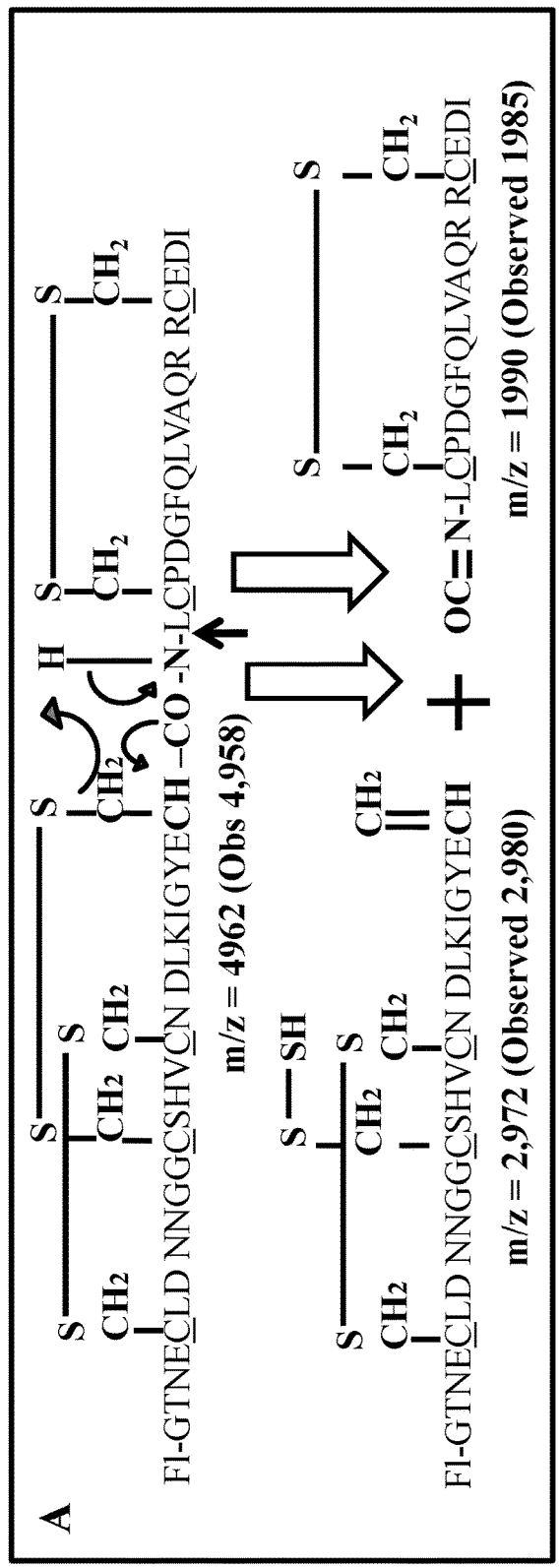
FIG. 6A illustrates the proposed mechanism for the cleavage of FI-EGF-A peptide during laser-based mass spectrometry. It shows the possible mechanism for the breakdown of FI-EGF-A peptide under high laser power condition during SELDI-tof mass spectrometry. All atoms are shown in bold characters whereas the amino acids (single letter code) are indicated in regular character with Cys residue underlined.
FIG. 6B illustrates a theoretical 3D model structure of FI-EGF-A peptide. It shows theoretical 3D energy minimised model structure of EGF-A peptide in vacuo based on Hyperchem software v11 program. The three S—S bridges present are indicated by arrows. The sequence is derived from hLDL-R (aa314-355).
Figure 6:
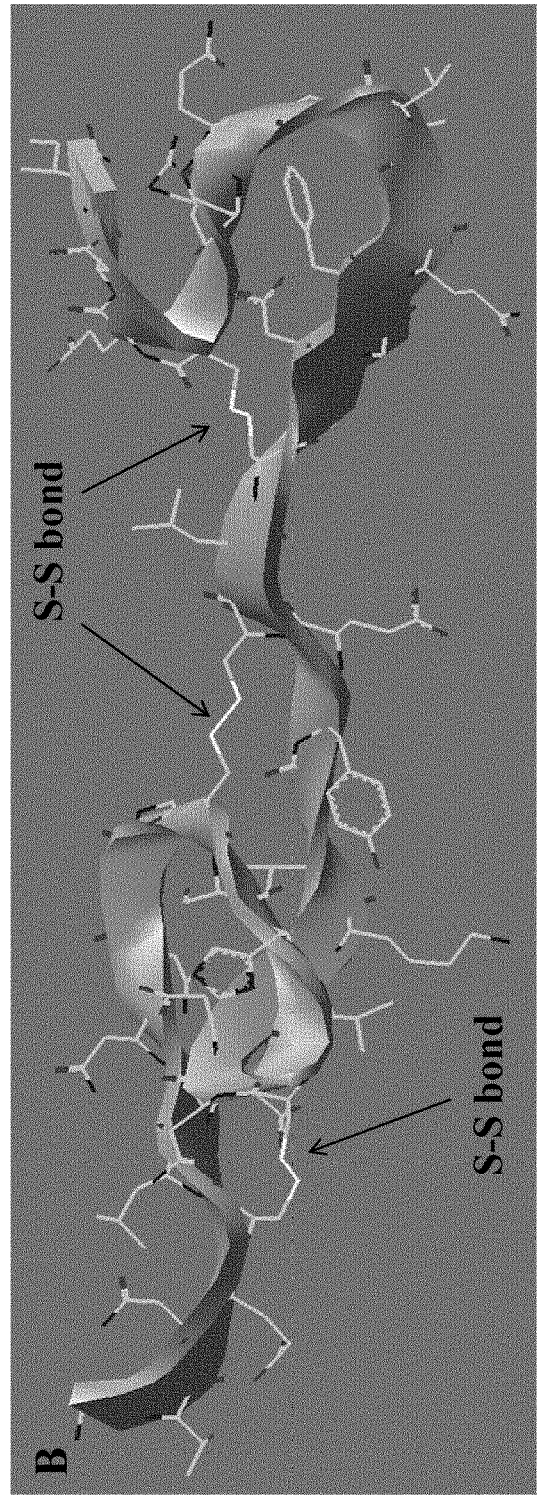

However following reduction with TCEP [Tris (2-carboxy ethyl) phosphine], it reacted with 6 molecules of iodoacetamide leading to hexa-acetamidyl derivative (increase of 6×57=342 Da in MW) as revealed by mass spectrum (not shown). This result confirmed the presence of 3 S—S bonds in the starting peptide. Furthermore it is noted that Fl-EGF-A upon high-power laser treatment during mass spectrum exhibited two additional broad peaks at m/z~2,980 and ~1,987. It is proposed that these two peaks are likely generated through breakdown of Fl-EGF-A molecule via a 6-member transition state mechanism as shown in FIG. 6A. This proposed fragmentation provided additional support to the structure and the presence of 3 S—S bridges as shown in (Ia). In a similar manner Bio-EGF-A (Ib) was also prepared by attaching biotin at the N-terminus and fully characterized. A 3D energy minimized model structure in vacuo based on Hyperchem v11 software program (FIG. 6B) revealed the rigid geometry of the molecule stabilized by 5-H-bonds, 2 within the S—S bond involving $Cys^{12}$ and $Cys^{25}$ Fl-Bio-Ahx-Lys-Methyl Ester (IIId)

This model bis-functional Lysine derivative was synthesized in 4 steps as described in FIG. 4, then purified by silica-gel chromatography and fully characterized by mass spectrometry (calculated MW=877 Da; Observed MW=878 ($M^+$+H).

Example 3

In Vitro Binding Study hPCSK9 Catalytic Peptides Vs Fl-EGF-A

Fluorescence Quenching.

Figure 7:
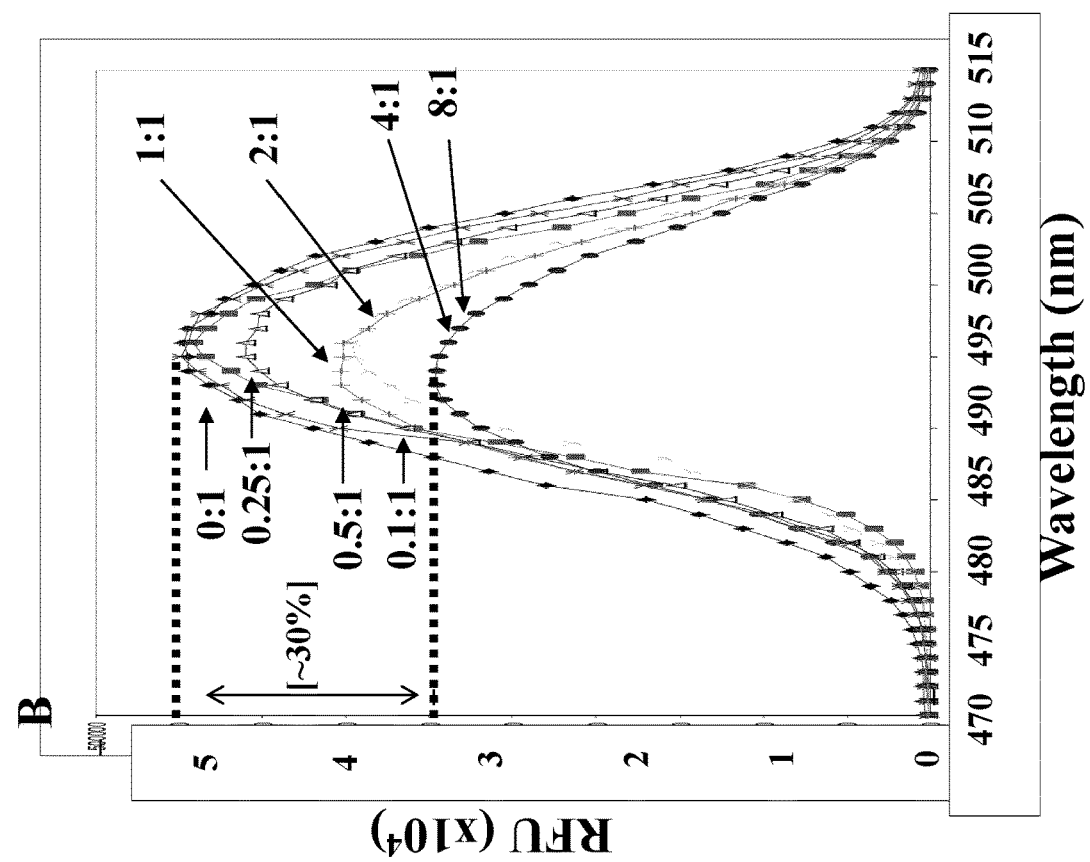
FIG. 7A illustrates fluorescence scan spectroscopy of FI-Bio-Ahx-Lys-Methyl ester (IIId) in presence of avidin. The figure shows overlaid emission fluorescence spectra of FI-Bio-Ahx-Lys-Methyl ester (IIId) in absence and presence of varying concentrations of avidin protein at $\lambda_{ex}$=520 nm.
FIG. 7B illustrates fluorescence scan spectroscopy of FI-Bio-Ahx-Lys-Methyl ester (IIId) in presence of insulin as control peptide. The figure shows overlaid emission fluorescence spectra of FI-Bio-Ahx-Lys-Methyl ester (IIId) in absence and presence of varying concentrations of standard h-insulin externally added as control, $\lambda_{ex}$=520 nm. For each experiment 5 µl of 0.5 mM (IIId) peptide in water was used.
Figure 7:
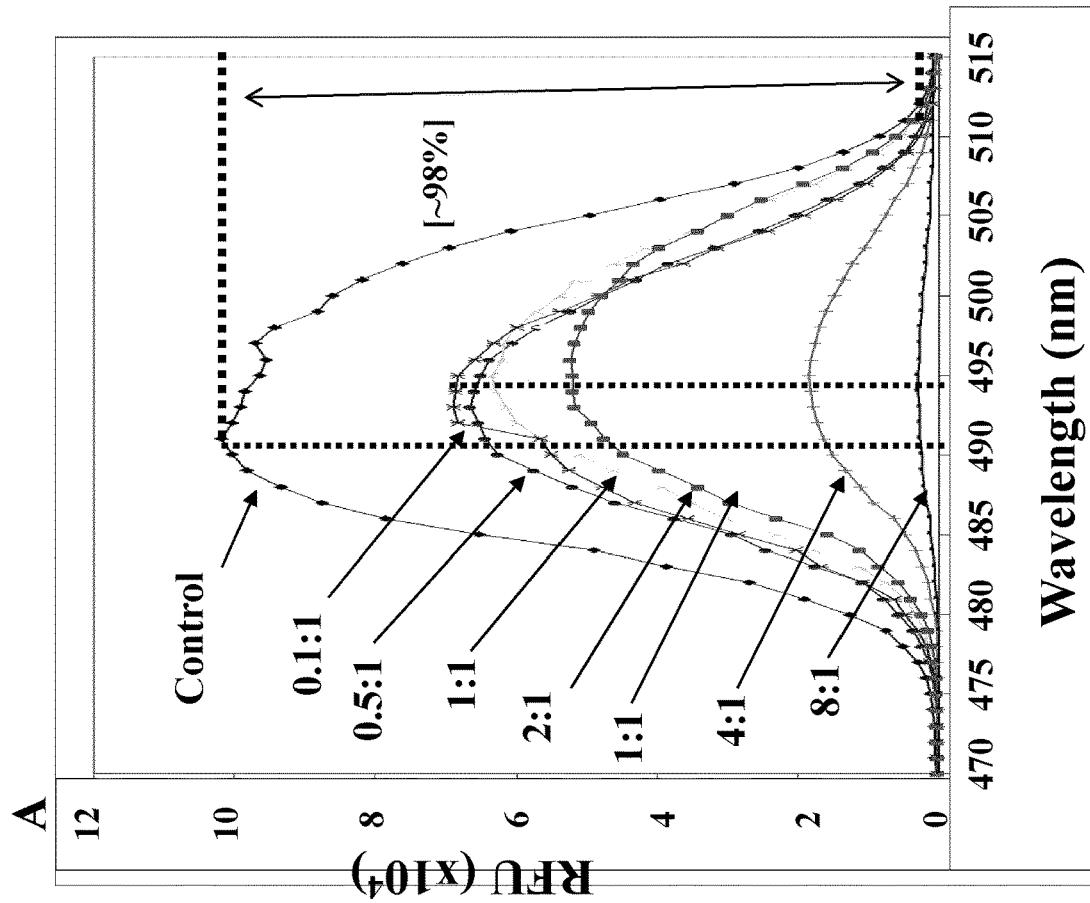

Previously a number of studies reported that the interaction between two ligands one of which is fluorescence labeled can be followed by studying fluorescence intensity. In general the fluorescence intensity is suppressed with or without shift of emission peak position when there is a strong interaction between the two ligands. Greater the suppression or quenching of fluorescence intensity, greater is the strength of binding. In order to further confirm the above notion, a study was carried out by using a fixed concentration of fluorescent biotinylated peptide (IIId) and increasing doses of avidin protein. As more and more avidin binds with biotin ($K_d$~$10^{-15}$ µm), a gradual suppression of fluorescence intensity was observed until it is ~98% quenched at 8:1 molar ratio of avidin:(IIId) (FIG. 7A). As expected similar results were also obtained with streptavidin ($K_d$~$10^{-4}$ µM), Captavidin ($K_d$~$10^{-15}$ µM) and Nutravidin ($K_d$~$10^{-15}$ µM) [Molecular Probes: The handbook, Chapter 7 available, Invitrogen Corporation] with maximal of ~81.4%, 75.5% and 85% quenching respectively (Data not shown). These avidin analogs with varying binding affinity towards biotin have been developed and made available through commercial organizations [Polyscience Inc., Technical Data Sheet Report-779]. On the contrary, when the same experiment was conducted with h insulin which does not bind with biotin, a maximum of only 30% quenching at 8:1 molar ratio of h insulin:(IIId) was noticed (considered as non-specific binding) (FIG. 7B). This study confirms that fluorescence quenching is an indicator of binding between two ligands one of which is fluorescently labeled.

Figure 8:
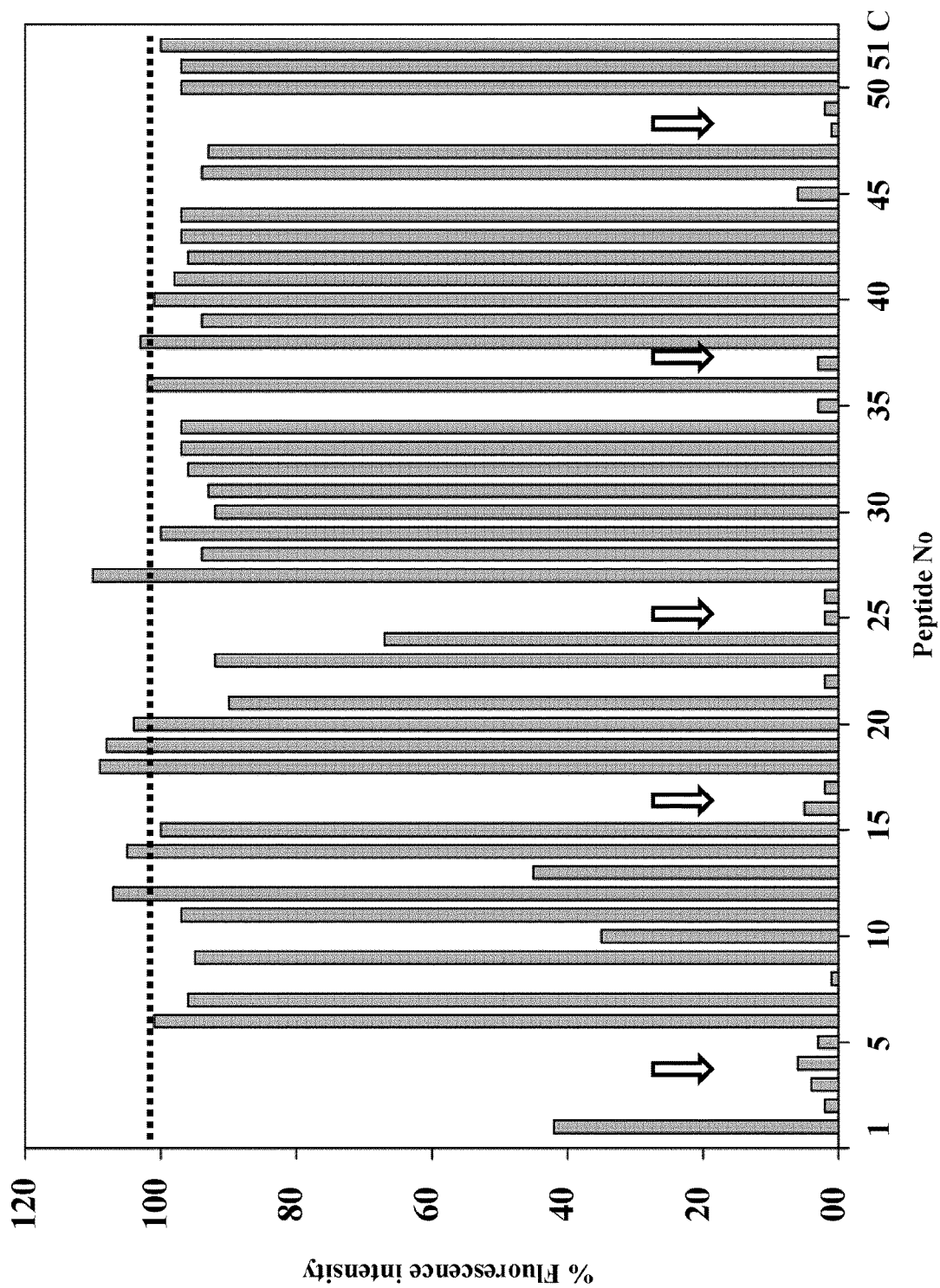
FIG. 8 illustrates the relative binding affinities of 51 PCSK9 peptides towards FI-EGF-A peptide using fluorescence quench method. The figure shows binding results of all 51 synthetic PCSK9 catalytic peptides towards FI-EGF-A peptide based on fluorescence quenching. The fluorescence intensity of FI-EGF-A peptide was measured following incubation for one hour with each peptide at $\lambda_{ex}$=492 nm, $\lambda_{em}$=520 nm. The values were compared with that of control (C) in the absence of any peptide. The down vertical arrows indicated strong fluorescence quenching effects by peptides no P2-P5, P8, P16, P17, P22, P25, P26, P35, P37, P45, P48 and P49. The dotted horizontal line in bold character indicates the control fluorescence intensity when there is no peptide added. As before for each experiment 5 µl of 0.5 mM FI-EGF-A peptide in water was incubated with 10 µl, 0.5 mM hPCSK9 peptide solution for 1 h. For control the peptide was substituted by 10 µl water.

Additional fluorescence quenching studies were conducted using FI-EGF-A peptide and each of the 51 synthetic hPCSK9 catalytic peptides, one at a time. The results are depicted in FIG. 8 which revealed strong fluorescence quenching effect in the presence of peptides P2-P5, P8, P16, P17, P22, P25, P26, P35, P37, P45, P48 and P49 (SEQ ID NOS: 2-5, 8, 16-17, 22, 25, 26, 35, 37, 45, 48 and 49) suggesting their interactions with FI-EGF-A but no conclusion could be made about their relative binding affinities.

Mass Spectrum.

Figure 9:
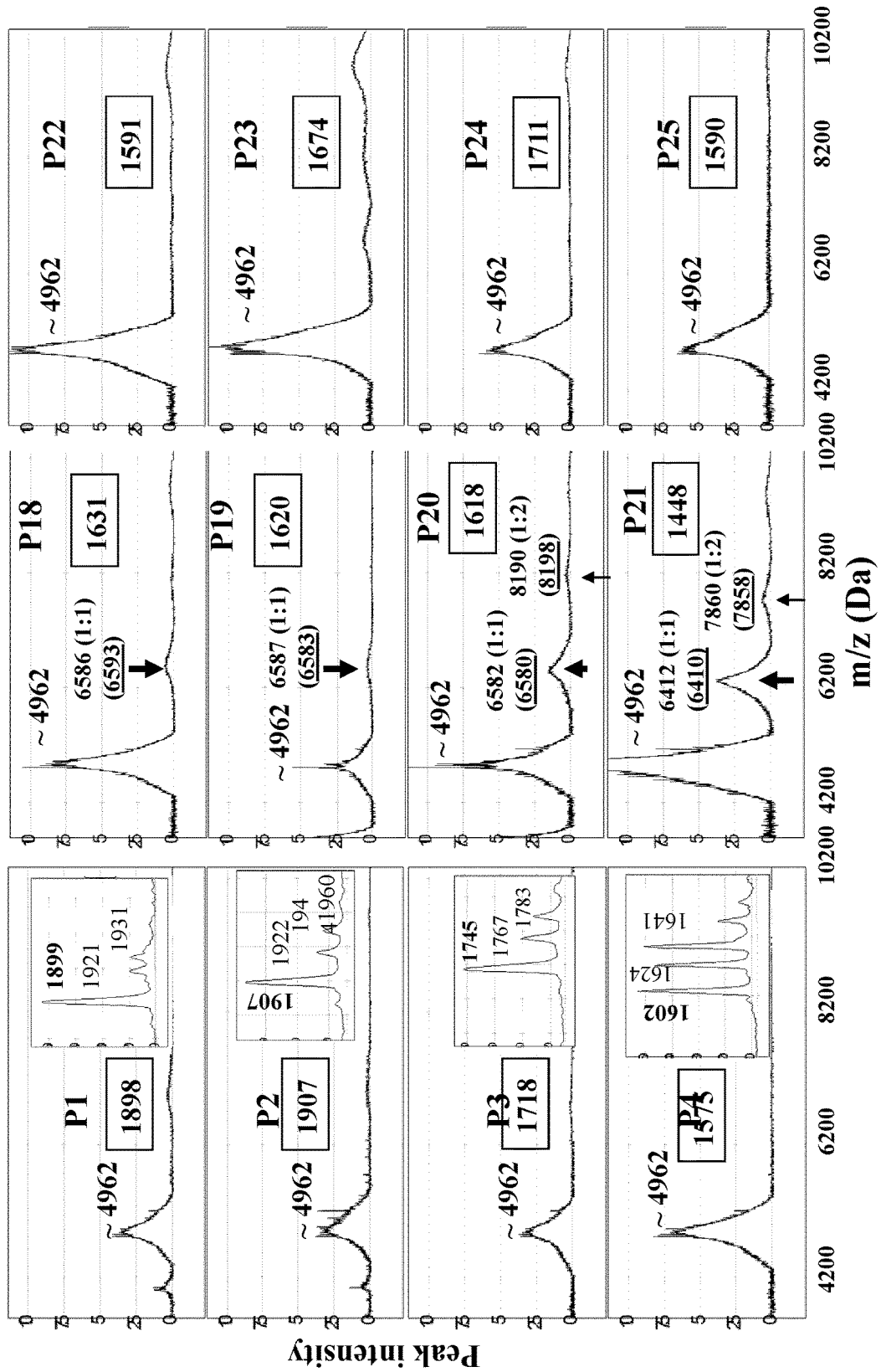
FIG. 9A illustrates the SELDI-TOF Mass Spectra of FI-EGF-A (Ib) following incubation with various PCSK9 catalytic peptides. The figure shows the mass spectrum of FI-EGF-A peptide (Ib) following incubation with selected PCSK9 catalytic peptides. Note the formation of a 1:1 complex between FI-EGF-A (Ib) (MW-4,962) and P18-P21 peptides leading to peaks in the mass spectrum at m/z 6,400-6,600 Da as indicated by thick vertical arrows. The thin arrows corresponded to the formation of 1:2 adduct formation (peaks ranging from ~7,800-8,200 Da; shown underlined for calculated value). The calculated MW values of individual PCSK9 catalytic peptides are shown within a box while their expanded MS profiles in selected cases were shown within the inserts in the MS figure.
FIG. 9B illustrates the SELDI-TOF Mass Spectra of FI-EGF-A (Ib) upon incubation with selected hPCSK9 catalytic peptides. Again 1:1 complex formation whenever observed was indicated by thick arrows while 1:2 complex formation was shown with thin arrows. The molecular weight of each peptide was shown within a box in the MS figure.
FIG. 9C illustrates the SELDI-TOF Mass Spectra of control FI-EGF-A (Ib) (in triplicates) with no added peptide as well as in presence of selected PCSK9 catalytic peptides. As expected the mass spectrum of control FI-EGF-A peptide showed a broad single peak at ~4,962 Da and no other peaks in the area ~6,000-8,000 Da where the peaks for the adducts should normally appear.
Figure 9:
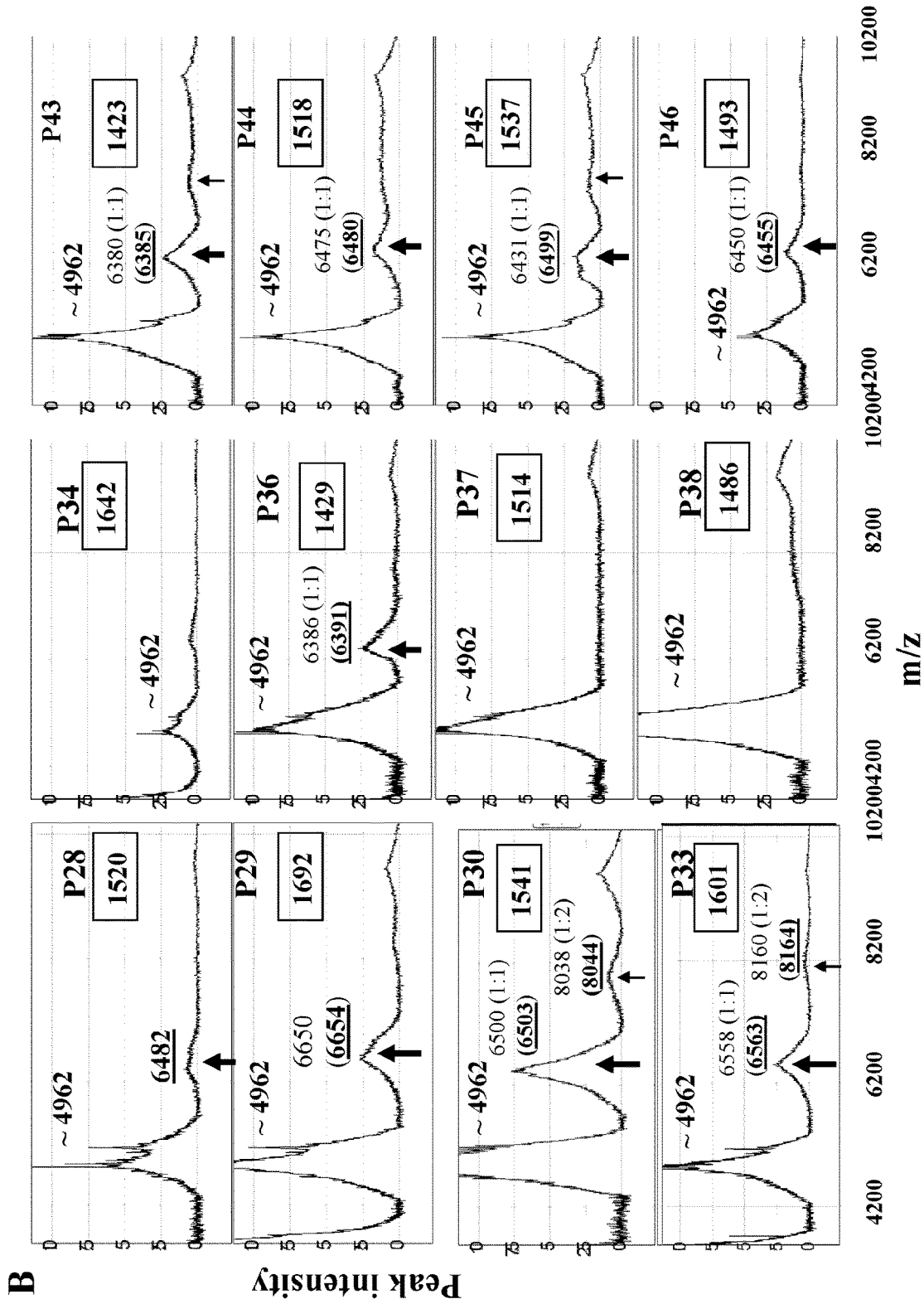
Figure 9:
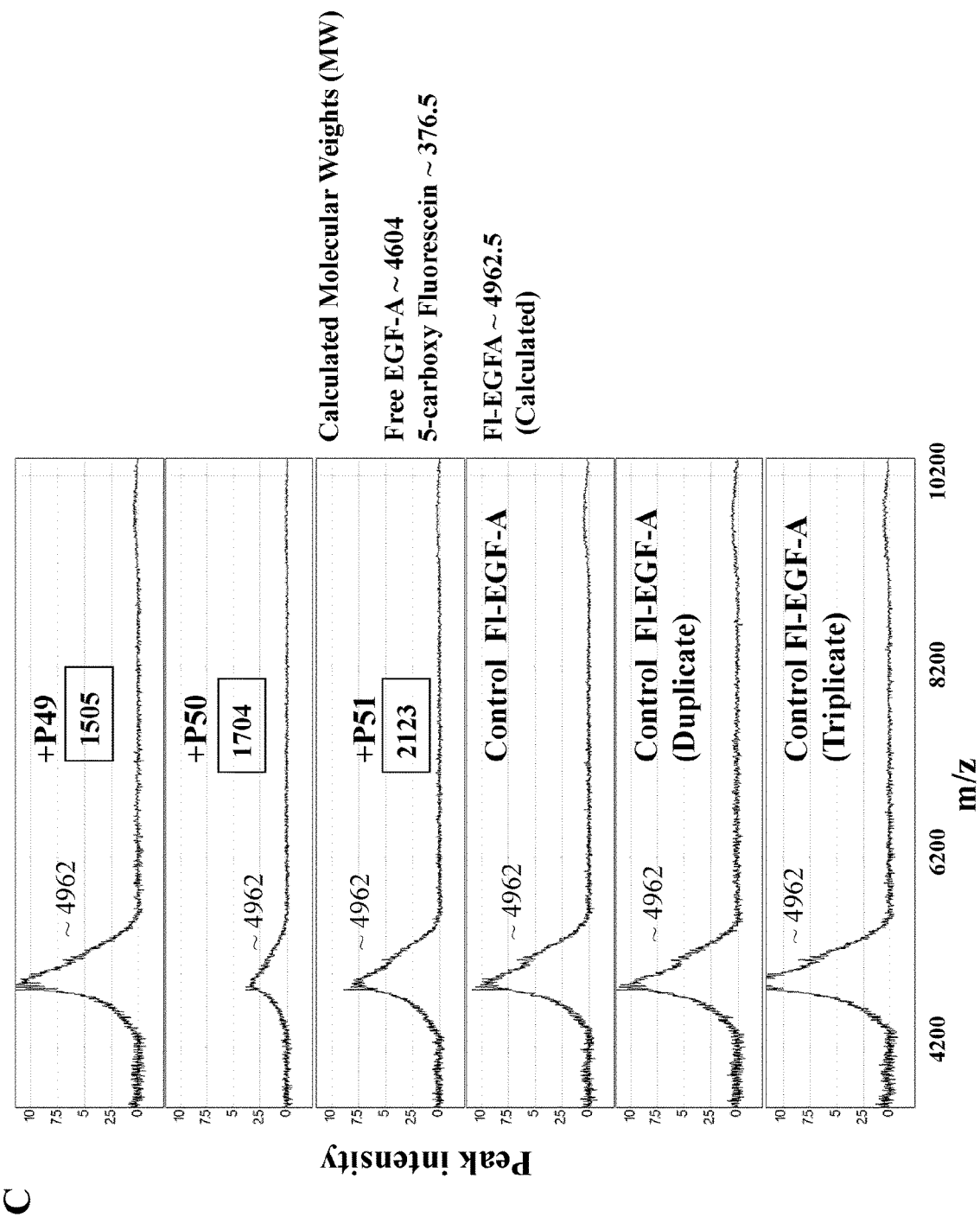

SELDI-Tof mass spectra of FI-EGF-A peptide following 1 h incubation with each of the 51 peptides (P1-P51, SEQ ID NOS:1-51) revealed formation of 1:1 and in some cases weak 1:2 adducts with selected peptides as shown in FIGS. 9A-C. It is noted that formation of such complexes or adducts were not observed as expected in the mass spectrum of FI-EGF-A alone (see FIG. 9C done in triplicate) and for samples with other peptides. It is likely that above non-covalent adducts were strong enough to survive dissociation during mass spectrometry laser bombardment. Overall the data suggested qualitative binding of FI-EGF-A with the peptides P18-P21, P28-P30, P33-P36 and P43-P46 (SEQ ID NO: 18-21, 28-30, 33-36 and 43-46). However the data did not reveal the comparative strength of binding of these peptides with FI-EGF-A peptide.

Native Gel Electrophoresis

Figure 10:
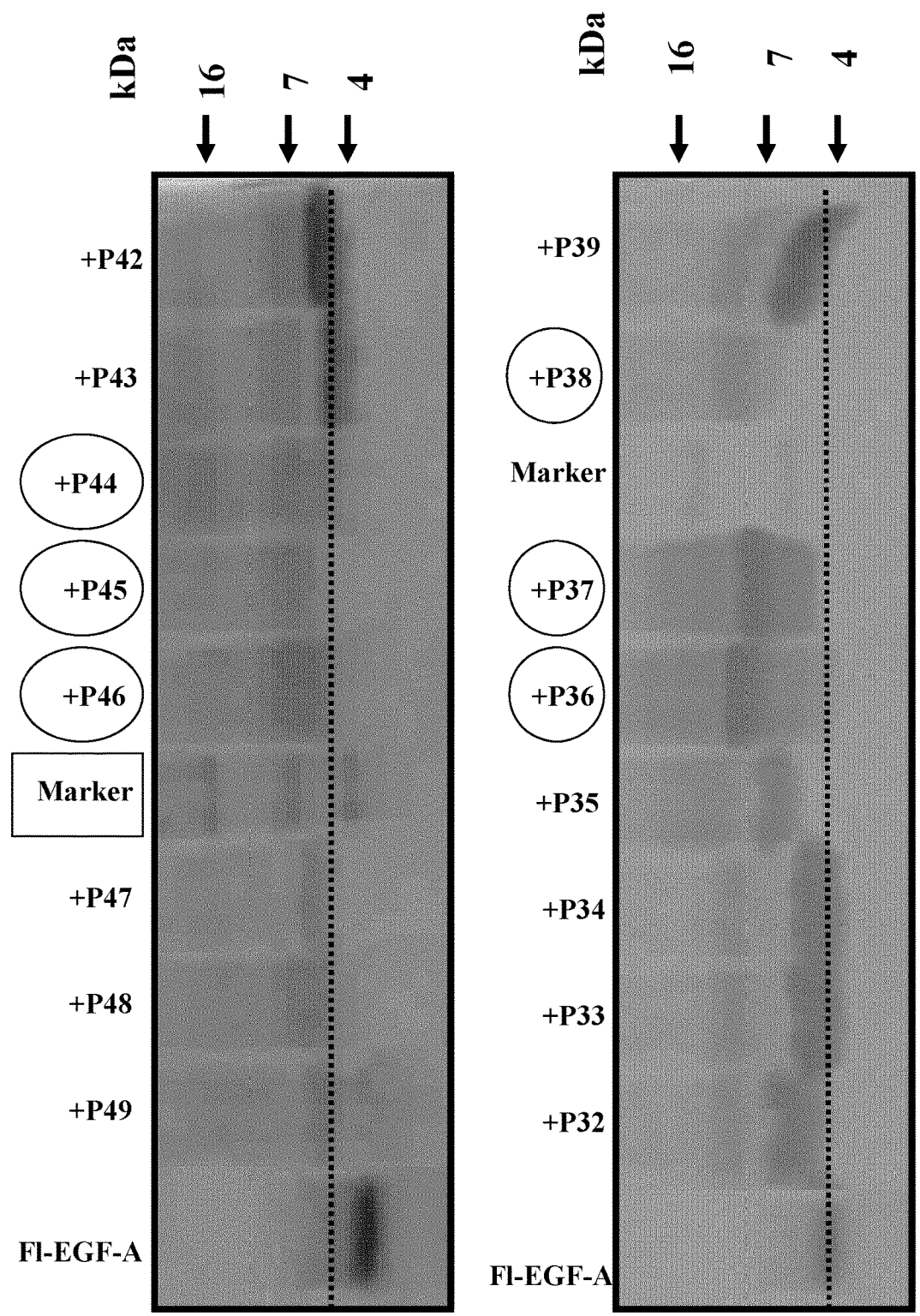
FIG. 10 illustrates native Gel Electrophoresis of FI-EGF-A (Ib) peptide showing adduct formation with selected PCSK9 catalytic peptides. The figure shows the native gradient gel electrophoresis of FI-EGF-A (Ib) peptide using 4-10-16% Tris/Tricine demonstrating the formation of 1:1 complex or adduct between FI-EGF-A (Ib) and selected PCSK9 catalytic peptides as highlighted by circles in the figure.

In order to gather further evidence for the above findings, native gel electrophoresis was performed on each incubated sample under SDS free non-denaturing condition in Tris-Glycine gel with appropriate standards as described [77]. The results were shown in FIG. 10 for some selected samples which showed that the peptides P32, P35-P38 and P44-P48 (SEQ ID NO: 32, 35-38 and 44-48) all form 1:1 stable adducts with FI-EGF-A peptide (MW~5 kDa) leading to the formation of an additional band at ~7 kDa—not seen in the control sample consisting of FI-EGF-A alone with no added peptide.

Example 4

Recombinant FLAG-HPCSK9 vs FL-EGF-A

Figure 12:
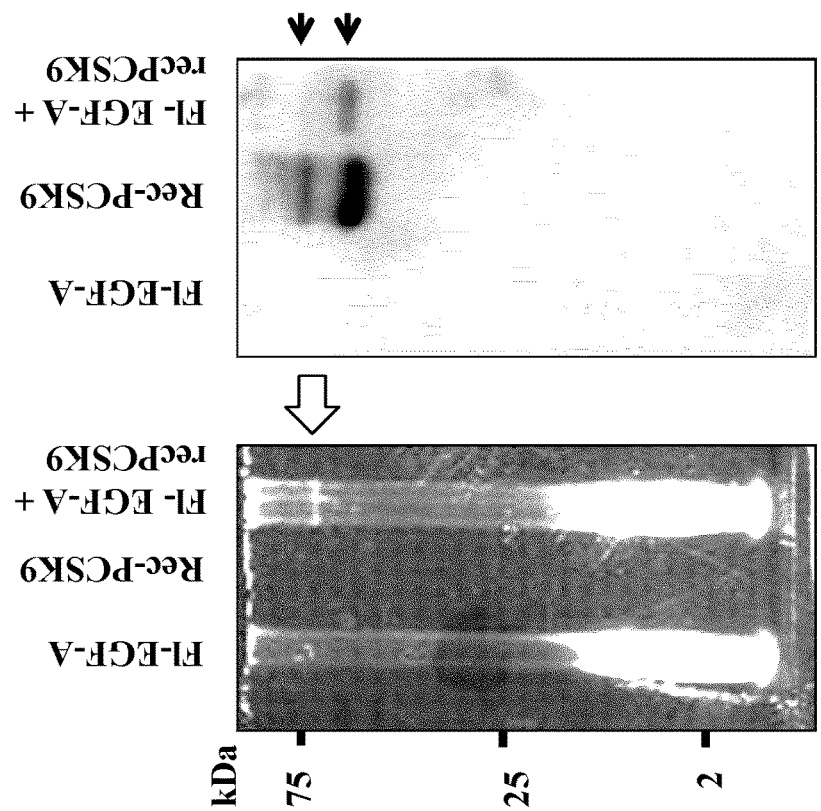
FIG. 12 illustrates SDS-Gel electrophoresis of FI-EGF-A peptide in presence and absence of recombinant hPCSK9 protein. 5 µg of FI-EGF-A (Ib) was incubated with 1 µg rec-hPCSK9 wild type (WT) for 2 h at room temperature. The samples were resolved in 10% SDS PAGE. Left: Fluorescence detection; Right: Western blot using anti-FLAG as primary antibody. There is a fluorescence positive band around 65 kDa (a mobility shift by ~5 kDa) shown by thick arrow indicating complex formation between 60 kDa rec-hPCSK9 mature form with 5 kDa FI-EGF-A (Ib) (Left panel). The right panel shows the western blot profile of rec-PCSK9 in presence and absence of FI-EGF-A peptide, Note the presence of two bands at ~74 (minor) and ~60 kDa (major) for proPCSK9 and mature PCSK9 proteins respectively. It is also noticed that after incubation with FI-EGF-A peptide, the 74 kDa PCSK9 protein is not recognized by anti-FLAG antibody while the 60 kDa hPCSK9 protein is still recognized but with reduced potency.
Figure 11:
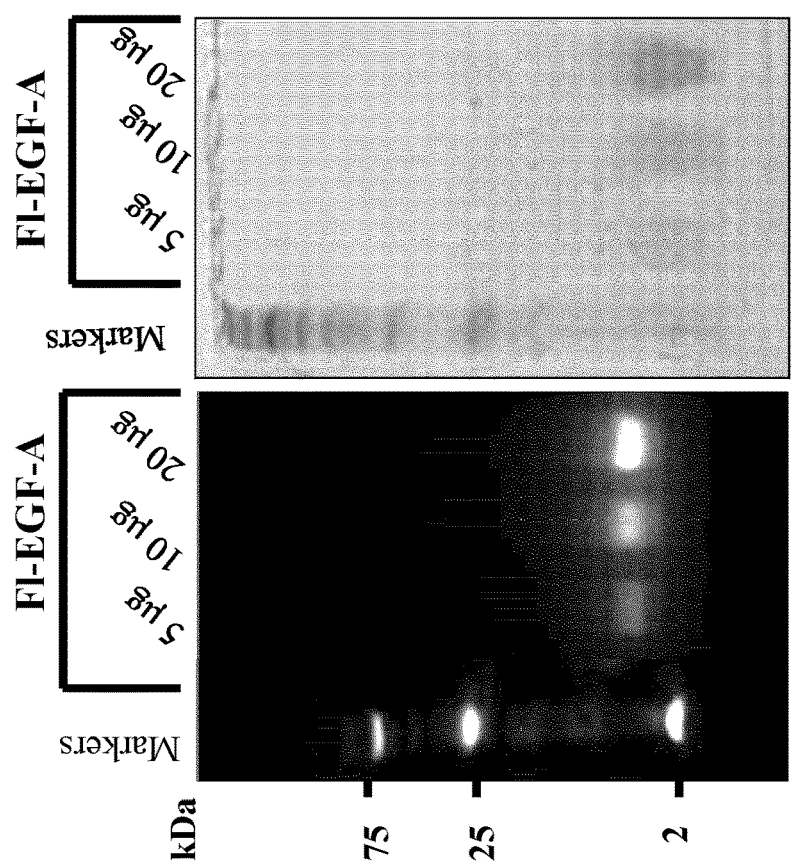
FIG. 11 illustrates SDS-Gel electrophoresis of FI-EGF-A peptide (Ib). Various amounts of FL-EGF-A (Ib) were resolved in a 15% SDS-PAGE and monitored by fluorescence intensity measurement (Left) and Coomassie staining (Right). Appropriate marker proteins (fluorescent and non-fluorescent) were also loaded on the gels for molecular weight determination purpose.

In addition to investigating the binding potential of PCSK9 catalytic peptides towards FI-EGF-A, affinity study for rec FLAG-PCSK9 protein against FI-EGF-A were also conducted. Purified rec-FLAG-PCSK9 protein WT or D/Y mutant were used. SDS-PAGE performed on FI-EGF-A peptide incubated alone and in the presence of recombinant FLAG-PCSK9 protein at various concentrations using fluorescence and coomassie staining detection methods were shown in FIGS. 11 and 12. As expected, FI-EGF-A exhibited a band at ~5 kDa consistent with its calculated MW which increases in intensity with dose in both fluorescence and staining intensity (FIG. 11). It may be pointed out that the exact position of the band for FI-EGF-A peptide as measured by fluorescence intensity (left) and coomassie stain (right) is in fairly good agreement and the minor difference noted were due to diffused nature of the band due to low molecular weight of FI-EGF-A (Mol Wt~5 kDa) in SDS-scale. When incubated with recPCSK9, FI-EGF-A exhibited a fluorescent positive band at ~65 kDa (indicated by a big arrow, FIG. 12, left panel) likely due to the formation of adduct between ~60 kDa mature recPCSK9 and ~5 kDa FI-EGF-A peptide. As expected this fluorescent band is absent in recPCSK9 alone lane which showed immunoreactive bands at ~74 kDa and 60 kDa for pro-PCSK9 and mature PCSK9 forms respectively when probed against anti-FLAG antibody (FIG. 12, right panel). The data shows that the recPCSK9 forms a stable complex with FI-EGF-A peptide but it is likely that only the mature PCSK9 (MW 60 kDa) binds with FI-EGFA to produce an adduct detectable by both fluorescence (left panel) and western blot (right panel). However, it is also possible that the pro-PCSK9 form (74 kDa) which is the minor one, may also bind to FI-EGFA but relatively weakly thereby not detectable by fluorescence at all. However it is detectable by western blot though with reduced intensity. This may be explained by the fact that upon binding with FI-EGFA, PCSK9 is recognized by FLAG antibody only with reduced potency. Unfortunately similar experiments could not be performed to study the interactions of various synthetic hPCSK9 peptides with FI-EGF-A since the expected MWs of each adduct (varying from ~6.3-7 kDa) are too close to the molecular weight of unbound FI-EGF-A peptide (~5 kDa) and therefore will be difficult to be detected in the large background of mass intensity of unreacted FI-EGF-A Example 5

Cell Culture Study

The above binding affinities of selected PCSK9 catalytic peptides and rec-PCSK9 protein towards FI-EGF-A peptide indicated that they may regulate LDL-R level when applied to the culture medium of growing hepatic cells such as HepG2 and HuH7 which express both PCSK9 and LDL-R. This expectation is based on the fact that binding of PCSK9 with LDL-R via latter EGF-A domain is the key event for LDL-R degradation.

Effect of FI-EGF-A on LDL-R in HepG2/HuH7 Cell Lines

Figure 13:
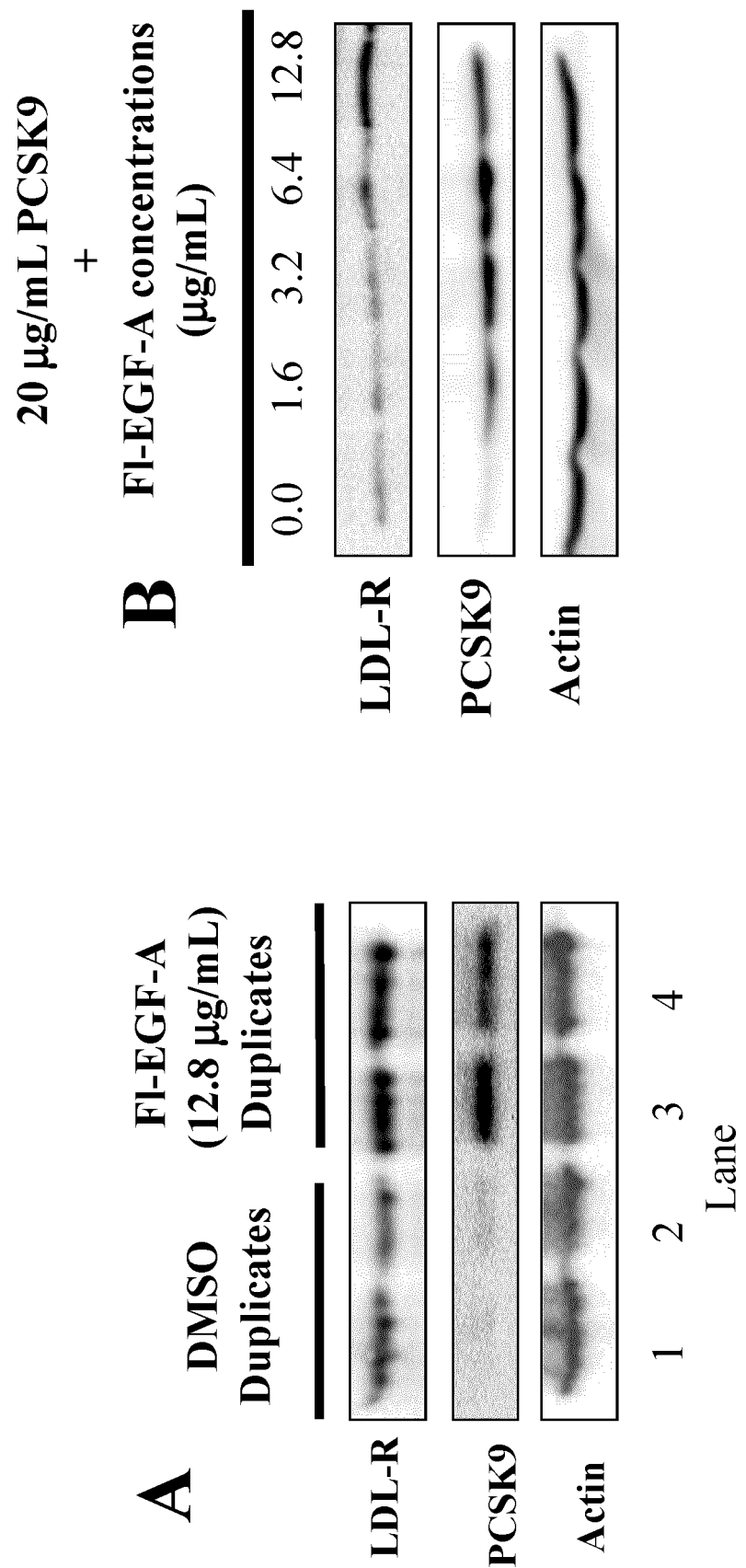
FIG. 13 illustrates (A) Western blot analyses showing the quantitation of LDL-R and PCSK9 levels under various conditions in HepG2 cells. These are western blot figures showing the effect of externally added FI-EGF-A peptide on exogenous levels of LDL-R and PCSK9 in growing HepG2 cells. The cells were harvested after 24 h and whole cell lysates were used for analysis of LDL-R, PCSK9 and actin levels both for control sample (DMSO) and FI-EGF-A done in duplicates. Actin was used as a house keeping control protein for quantitation purpose. (B): Rescue effect of FI-EGF-A peptide added in increasing concentration levels on LDL-R in growing HuH7 cells in the presence of added rec-PCSK9 protein. Rec-PCSK9 was incubated with various amounts of Fl-EGF-A for 3 h at room temp and then applied to cells growing in 2 mL media to the concentrations as indicated in the figure. The cells were harvested 7 h later.

The first set of results are shown with FI-EGF-A in FIG. 13A which demonstrates that a 24 h treatment of HepG2 cells with this peptide solution in DMSO (12 µg/ml) resulted in a significant up regulation of the LDL-R (lanes 3 and 4) as compared to control treated only with DMSO (lanes 1 and 2). The results were based on western blot analysis of whole cell lysates as standardized against the house-keeping protein actin. The above effects were accompanied by a marked up regulation of PCSK9 suggesting an auto regulatory feedback loop. It also suggested that the actual effect may be much more significant than what is revealed by western blot data (FIG. 13A). To further confirm the data and to find out whether our synthetic FI-EGF-A peptide is capable of restoring LDL-R level following it's degradation by PCSK9, we added rec-PCSK9 (20 µg/ml) to the culture medium of growing HuH7 cells in the absence and presence of increasing amounts of FI-EGF-A peptide. The results are shown in FIG. 13B by western blot analysis for PCSK9, LDL-R and actin contents in cell lysates. The data suggested that following addition of recPCSK9 protein, LDL-R level as expected decreased significantly which was then partly restored gradually upon addition of FI-EGF-A peptide in a dose-dependent manner.

Example 6

Effect of hPCSK9 Catalytic Peptides on LDL-R in HepG2 Cells

Next we examined the effects of all 51 hPCSK9 catalytic peptides on LDL-R and PCSK9 levels in HepG2 cells using a fixed ~5.5 μM concentration level which was found to be most optimum and non-toxic based on MTT test (data not shown) and other data which revealed that most peptides begin to exhibit toxic effect at >25-50 μM, depending on the peptide's nature. The data based on western blot analysis of cell lysates for LDL-R and PCSK9 as compared to the house keeping protein Transferrin Receptor (TR), suggested that the peptides P35-P39, P42, P43, P46 and P47 (SEQ ID NOS: 35-39, 42, 43, 46 and 47) differentially enhance LDL-R level without significantly affecting PCSK9 level (FIGS. 14A-C). Interestingly addition of an equimolar mixture of two peptides often results in synergistic effect on LDL-R promoting activity. So far the highest synergistic LDL-R promoting activity (~3-fold higher than control) was noted with P36 and P37 mixture (SEQ ID NOS: 36-37) (FIG. 14C). This is followed by P36+P47 (SEQ ID NOS: 36 and 47) and P36+P42 (SEQ ID NOS: 36 and 42) mixture respectively. This likely suggests that P36/P37 as well as P46/P47 segments were equally effective in promoting LDL-R level based on HepG2 cell study.

Example 7

Design of S—S Bridge Loop Peptides from PCSK9 Catalytic Domain

Figure 15:
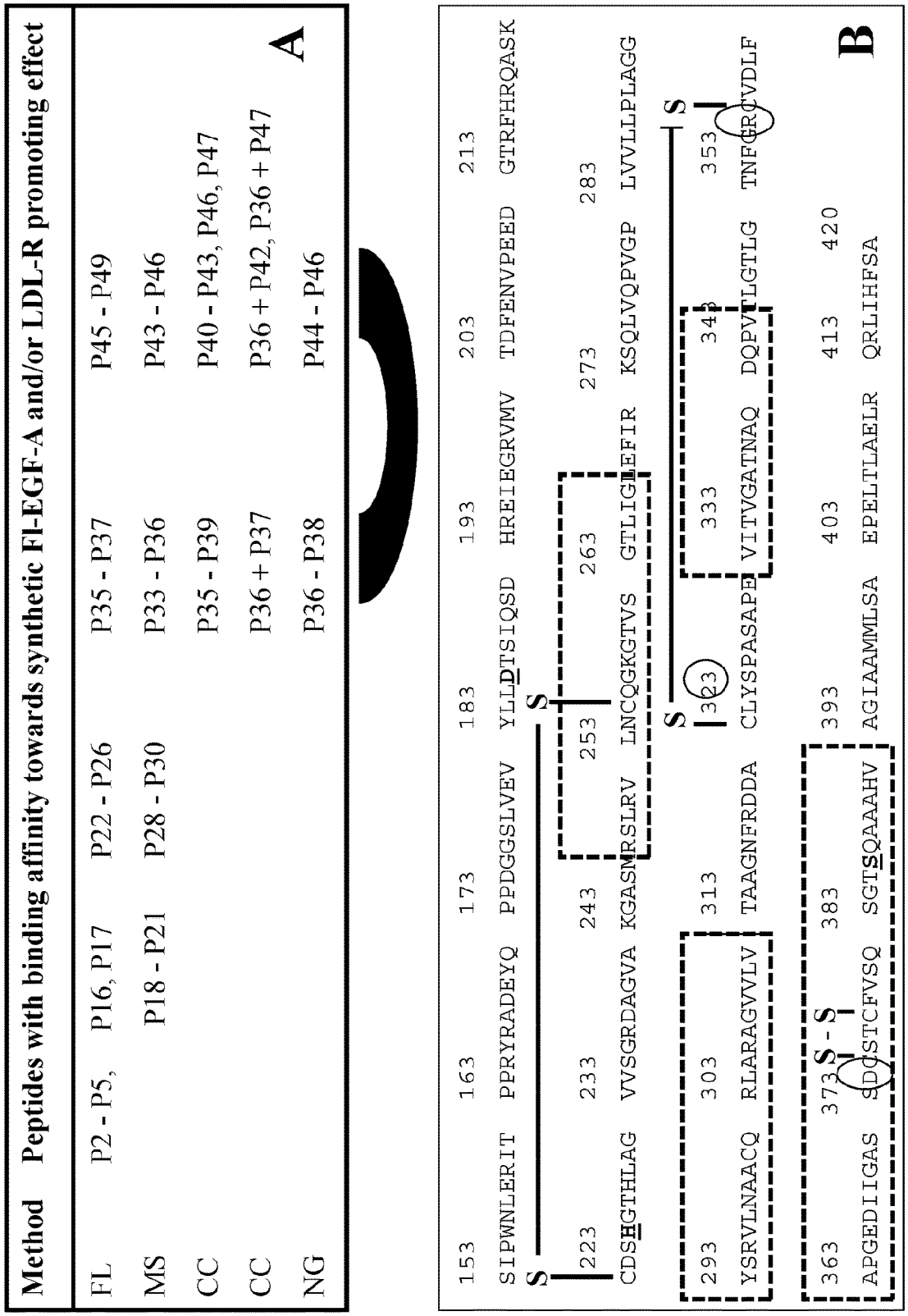
FIG. 15 illustrates (A): List of PCSK9 peptides with Fl-EGF-A binding and/or LDL-R promoting activities based on various methods. FL=Fluorescence quench, MS=Mass spectrometry; CC=Cell culture; NG=Native gel. Two most potent gain of function mutations $D^{374}/Y$ and $R^{357}/H$ are shown with circles. (B): Location of above peptides within dotted boxes. S—S bridges with solid lines. Catalytic residues D, H & S are in bold underlined character.

So far all results taken together (summarized in FIG. 15, top panel) suggest that four specific peptide segments of hPCSK9 catalytic domain as indicated exhibit modest to strong binding affinity towards synthetic FI-EGF-A derived from LDL-R. Peptides derived from these segments possess LDL-R promoting activity in varying degrees based on studies in culturing HepG2 and HuH7 hepatoma cells. The precise location of these peptides within the catalytic domain of PCSK9 is shown in FIG. 15, bottom panel. There are three S—S bridge loop domains that consist of (aa223-255) (Loop-1), (aa323-358) (Loop-2) and (aa363-392) (Loop-3). Interestingly the two most potent LDL-R promoting peptide groups (~P34-P37) and (~P44-P47) (SEQ ID NOS: 34-37 and 44-47, respectively) were found to be located within Loop-2 and Loop-3 regions which also bear the two most potent gain of function mutations namely $R^{257}/H$ and $D^{374}/Y$ respectively.

Figure 16:
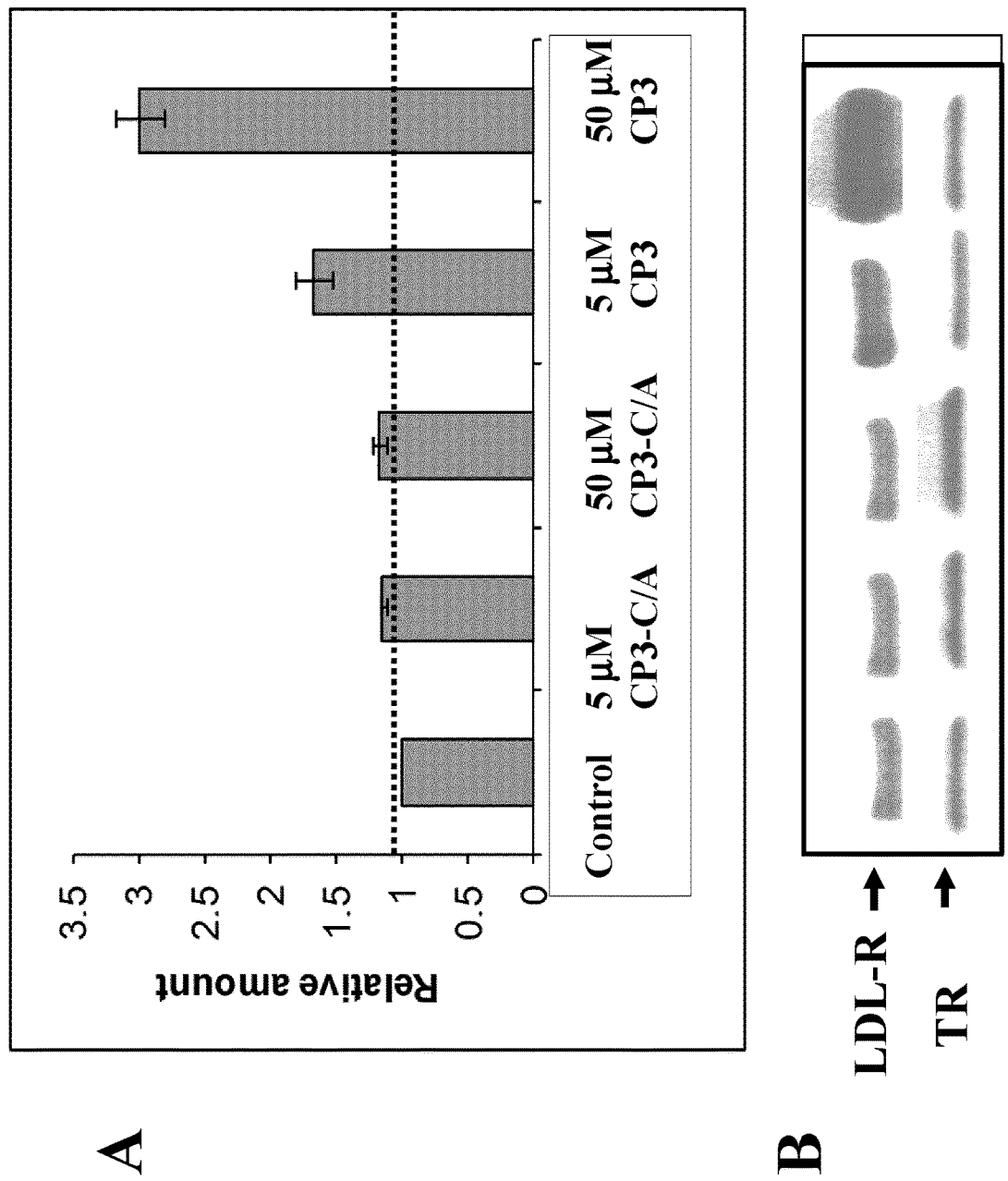
FIG. 16 illustrates the effects of PCSK9 catalytic cyclic Loop-3 Peptide (CP3) and its acyclic Ala-mutant on LDL-R in HepG2 cells. The figure shows western blot analyses for endogenous LDL-R and the control the house keeping protein TR (Transferrin receptor) in cell lysates following treatment with peptides at two different concentrations as indicated. Bar graphs show the relative amounts of LDL-R with respect to TR.

The presence of S—S bond may be crucial in terms of binding to LDL-R as it imparts a rigid structure and conformation to the molecule. In order to examine this notion and to develop even more potent LDL-R promoting agents, we synthesized S—S bridged cyclic $hPCSK9^{365-384}$ (CP3) and noncylic Cys/Ala mutant (CP3-C/A) (Table 2). These peptides were tested at 5.5 μM concentration as before in HepG2 cells for their effects on LDL-R. FIG. 16 showed that S—S bridged cyclic CP3 peptide at 50 μM promoted LDL-R level by ~3.5-fold (the highest so far) when added to growing HepG2 cells. This effect is completely lost for the corresponding acyclic peptide where Cys is substituted by Ala (CP3-C/A), suggesting the crucial role of S—S bond derived cyclic structure in LDL-R promoting activity.

TABLE 2

S-S bridged cyclic loop-3 peptide derived from the catalytic domain of hPCSK9 and its acyclic Ala mutant as indicated.

| Name | Position | Amino acid sequence |
|---|---|---|
| CP3 (Loop-3 peptide) | Cyclic-$hPCSK9^{365-384}$ | $^{365}$GEDIIGASS*D*CSTCFVSQSG$^{384}$<br>　　　　　　　S—S |
| CP3-C/A Loop-3 Ala-Mutant | Cyclic-$hPCSK9^{365-384}$ | $^{365}$GEDIIGASSDASTCFVSQSG$^{384}$ |

The crucial $D^{374}$ whose natural mutation to Y leads to the most potent gain of function and severe hypercholesterolemia, is depicted in bold italics character. The Cys pair with S—S connection as well as the mutation [$Cys^{375}$ to Ala (bold underlined)] were indicated in the figure.

Example 8

3D Model Structure of CP3

Figure 17:
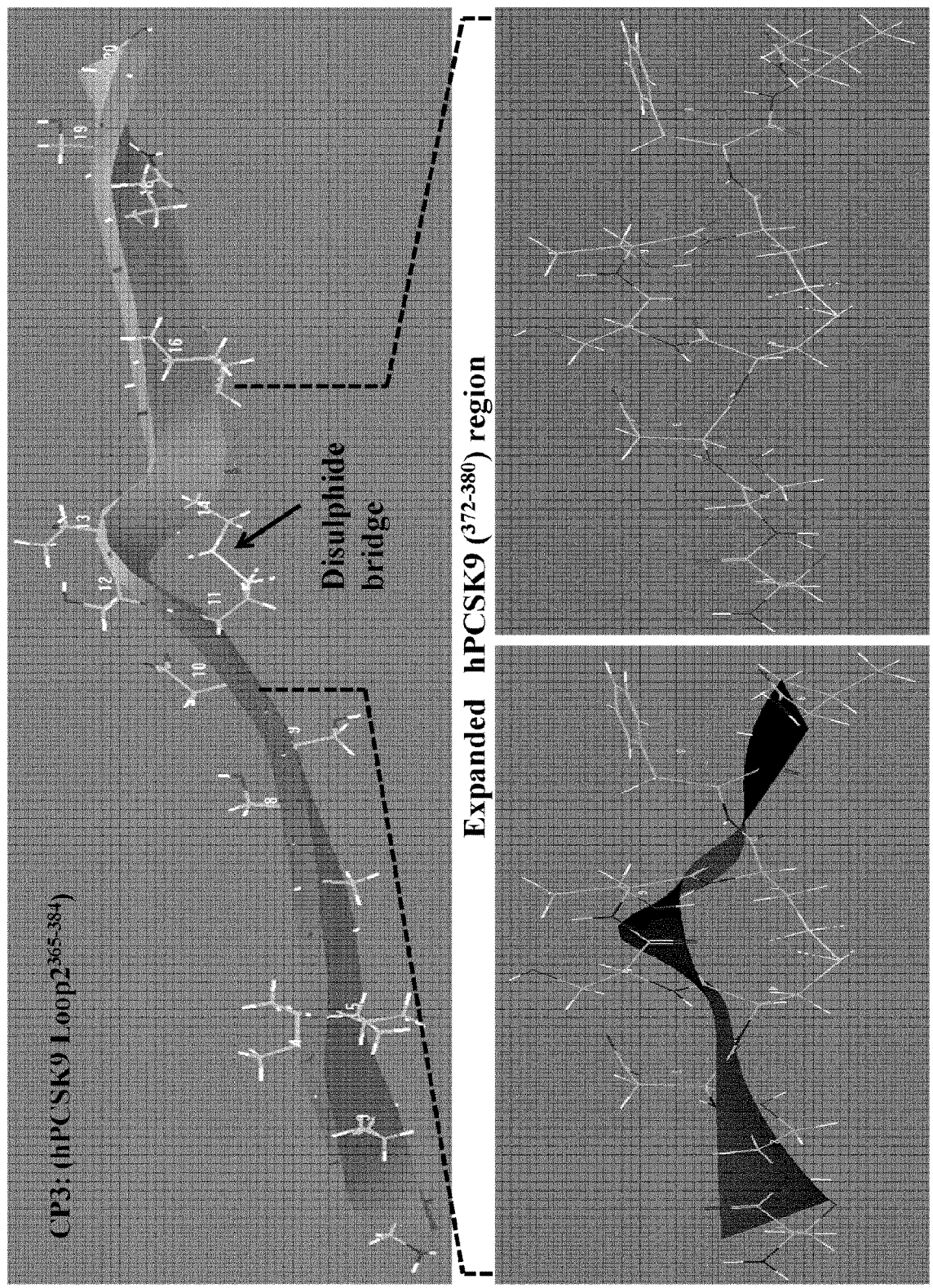
FIG. 17 illustrates the Energy minimized 3D model structure of CP3 peptide derived from hPCSK9 catalytic domain. This theoretically derived structure for disulphide bridged cyclic peptide CP3 [hPCSK9$^{365-384}$: $^{365}$GEDII-GASSDCSTCFVSQSG$^{384}$) was generated in vacuo by using algorithms based on Hyperchem v11 software program. An expanded figure covering the central region (aa372-380) is also shown in the figure at the bottom section. The two key Cys residues implicated in S—S bridges forming a cyclic structure are shown in the figure.
Figure 18:
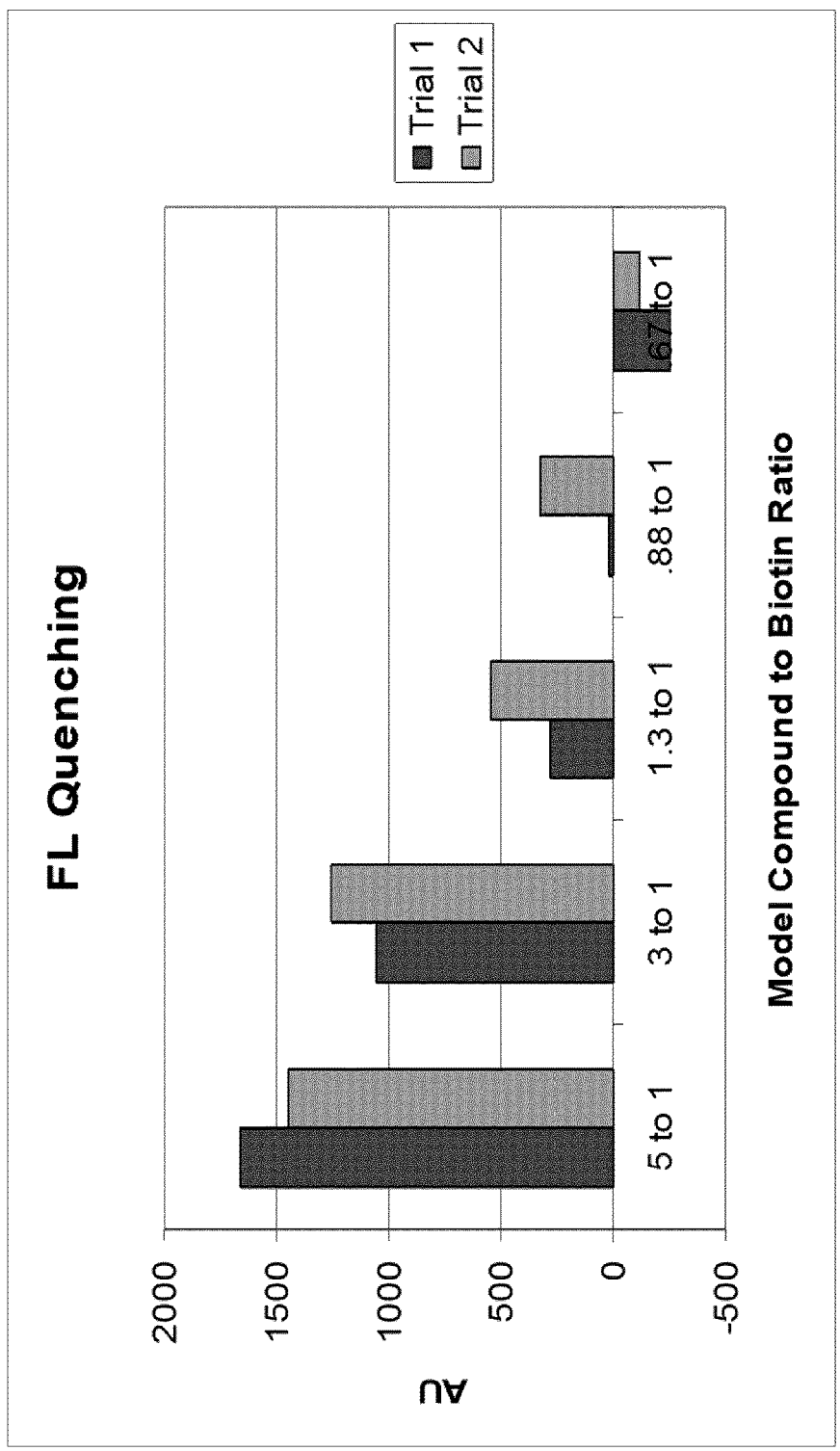
FIG. 18 illustrates Raw fluorescence unit (RFU) values of Fl-Bio-Ahx-Lys-Me-ester (IIId) measured at fixed $\lambda_{ex}$=520 nm and $\lambda_{em}$=492 nm (Duplicates) in the absence and presence of increasing concentrations of avidin protein as follows: Avidin:(IIId)=0.7:1, 0.9:1, 1.3:1, 3:1 and 5:1.

Owing to the critical role of S—S bond on biological activity (LDL-R promoting) as observed with CP3, we conducted 3D molecular model analysis of this peptide using Hyperchem v 11.0 software program (FIG. 17). The figure revealed that CP3 within its central core structure contains a small loop consisting of 14-atoms. This theoretical geometry developed in vacuo is supported by 2-H-bonds as indicated by dotted lines. With Ala-mutant this structural feature is lost which may contribute to the loss of LDL-R promoting activity.

Example 9

Discussion

LDL-R Binding Linear and Cyclic Peptides from hPCSK9

Figure 14:
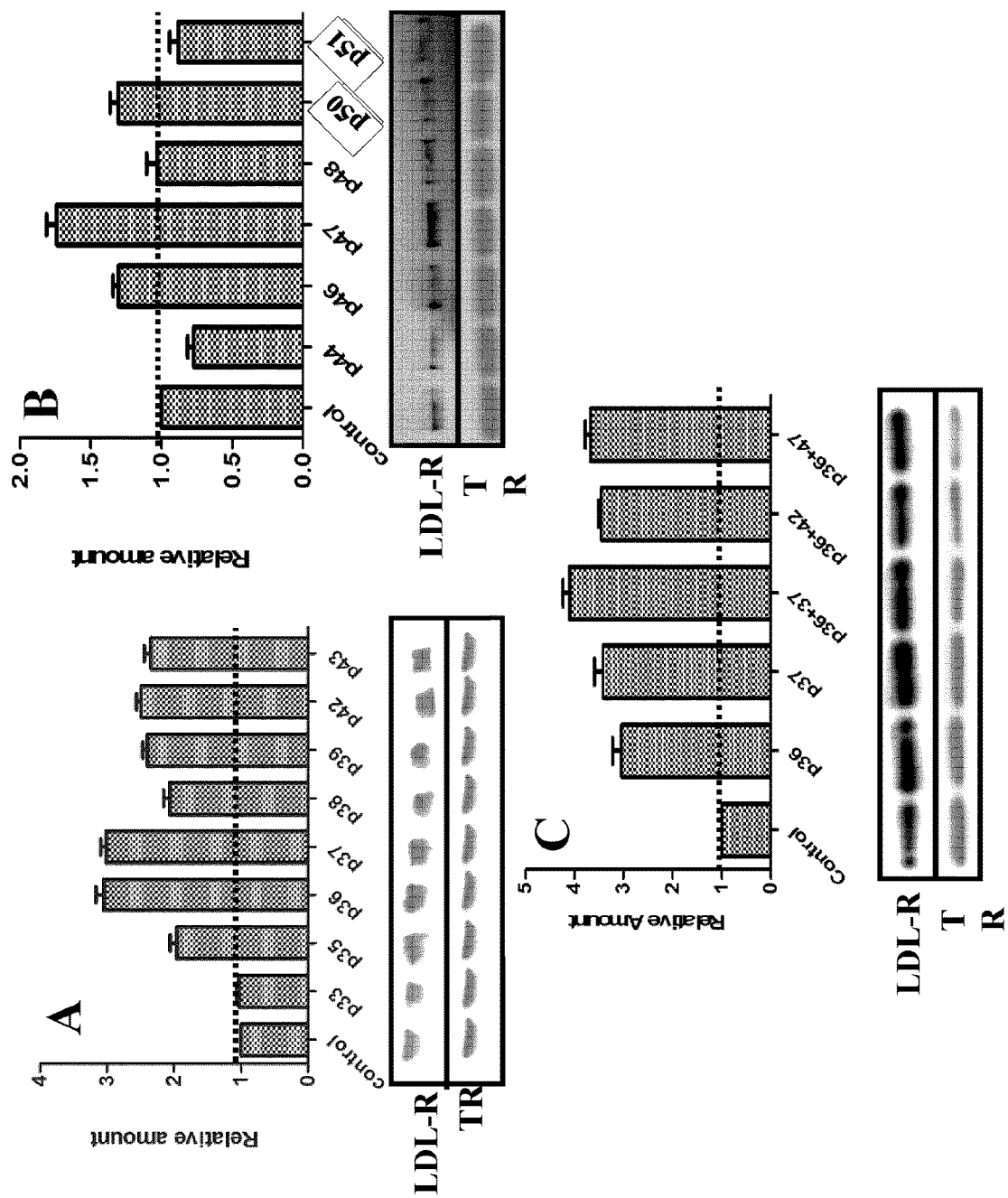
FIG. 14 illustrates Western blots showing PCSK9 and LDL-R levels in the presence of various PCSK9 catalytic peptides in HepG2 cell. The figure shows the effect of various PCSK9 catalytic peptides on LDL-R level when added individually at 5.5 µM concentration to the culture media of growing HepG2 cells. (A): P33-P43; (B): P44-P51 & (C): P36, P37 alone or in mixture with P42, P47 peptide respectively

Using 51 synthetic linear peptides covering the entire catalytic sequence of hPCSK9 (aa153-421) and various in vitro studies based on mass spectrometry, fluorescence quench method and Native-gel electrophoresis as well as western blot based cellular studies indicated that multiple specific peptide segments of hPCSK9 catalytic domain bind to synthetic 42-mer EGF-A peptide mimicking hLDL-R (aa314-355). This sequence has been implicated in the binding of LDL-R to PCSK9 catalytic domain as established by various studies including the crystal structure [Piper D E et al. The crystal structure of PCSK9: A regulator of plasma LDL-cholesterol. *Structure* 15:545-552, 2007]. Although these studies are not fully consistent with one another in terms of their ultimate binding conclusions (FIG. 15A), but the strong binding interaction of at least two domains characterized by the peptides ~P35-P39 and P44-P46 (SEQ ID NOS: 35-39 and 44-46 respectively) of hPCSK9 have been found to be supported by all the studies. In addition these peptides as expected also exhibited LDL-R promoting activity when added exogenously to growing HepG2 and/or HuH7 cells. In addition when some of these peptides are added in combination to the cells, a synergistic promoting effect on LDL-R has been noted (FIG. 14). This observation suggested that there exist multiple domains (at least 2)

within PCSK9 catalytic region which bind to EGF-A leading to enhancement of LDL-R level in cells.

Upon close examination of the location of these active peptides within hPCSK9 catalytic segment, it appears that they actually represent two S—S bridge cyclic loop domains of the protein (FIG. 15B). Sequence revealed that hPCSK9 catalytic domain (aa153-421) contains 7 Cys residues, namely at 223, 255, 301, 323, 358, 375 and 378. Among these, crystal structure and modeling studies revealed the following S—S bonds (aa223-255), (aa323-358) and (aa375-378) with the connectivity of $Cys^{301}$ remained unknown. Thus hPCSK9 catalytic segment is characterized by the presence of three S—S loop domains termed as Loop-1 ($C^{223}$—$C^{255}$), Loop-2 ($C^{323}$—$C^{358}$) and Loop-3 ($C^{375}$—$C^{378}$). Among them, Loop-3 contains a short cyclic structure and creates a small bump in the backbone structure. This structural feature appears more crucial and interesting. Moreover it also encompasses the sequence represented by P44-P47 peptides (SEQ ID NOS: 44-47) which individually promotes LDL-R level when added to growing HepG2 cells at a fixed concentration.

Our designed Loop-3 peptide, CP3 (having sequence SEQ ID NO: 56), exhibited a modest but significant LDL-R promoting activity when it was exogenously added to the culture medium of growing HepG2 cells at 5.5 µM concentration (FIG. 16). It is likely that this physiological effect is mediated via its competing effect with PCSK9 catalytic domain for LDL-R. This leads to reduced ability of PCSK9 to interact with LDL-R and degrade the latter. It will thus result in less LDL-C accumulation in the blood serum and thereby provide intervention of hypercholesterolemia—a serious risk factor of cardiovascular disease. It may also be pointed out that crystal structures of hPCSK9 bound to LDL-R or its derived EGF-A peptide revealed physical contact and interaction of various amino acid residues of EGF-A with $D^{374}$ and $F^{379}$ residues of hPCSK9 catalytic domain. In addition to these two amino acids, $R^{194}$ of hPCSK9 also plays a critical role in binding with EGF-A domain of LDL-R involving its $D^{331}$ residue located within EGF-A domain of LDL-R ($ND^{331}$ LK, see peptides Ia/b). Interestingly both $D^{374}$ and $F^{379}$ residues of hPCSK9 are present within CP3 sequence and this may explain its observed LDL-R promoting activity.

So far the data and findings are based upon binding experiments using synthetic EGF-A peptide.

Mutation and Consequence

This study identified the S—S bond containing cyclic loop peptide, $hPCSK9^{365-384}$ (CP3) as a potent region that can enhance LDL-R level upon its exogenous administration to the culture medium of growing HepG2 or HuH7 cells. Using 50 µM concentration of CP3, a ~3.5-fold increase in LDL-R level was observed (FIG. 16). It is also noted that this peptide can rescue LDL-R level to a significant level following its degradation by external addition of PCSK9 protein. This is highly significant and promising since it has the potential in clearing more LDL-C from circulation and may represent a lead peptide sequence for further future study towards development of small molecule PCSK9 inhibitors as non-statin alternative cholesterol lowering agents. The rigid cyclic geometry of this peptide and its model structure so crucial for its bio-activity may be utilized for development of future nonpeptide PCSK9 based cholesterol suppressing agents. In this connection, it is interesting to highlight that the above peptide sequence contains two key PCSK9 gain of function mutations namely $D^{374}$/Y and $R^{357}$/H sites which one can take advantage of for future development of more potent PCSK9 inhibitors.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. The isolated or purified therapeutically effective hPCSK9 polypeptide, consisting of the amino acid sequence of any one of SEQ ID NOS: 42 to 47, and SEQ ID NO: 56.

2. The isolated or purified therapeutically effective hPCSK9 polypeptide consisting of the amino acid sequence of any one of SEQ ID NO: 42, SEQ ID NO: 43, SEQ ID NO: 47, SEQ ID NO: 56 or combinations thereof.

3. The isolated or purified therapeutically effective hPCSK9 polypeptides of claim 2, consisting of the combination of the amino acid sequence SEQ ID NO: 36 and SEQ ID NO: 42 or SEQ ID NO: 36 and SEQ ID NO: 47.

4. An isolated or purified therapeutically effective hPCSK9 polypeptide consisting of the amino acid sequence of SEQ ID NO: 56:

Gly—Glu—Asp—Ile—Ile—Gly—Ala—Ser—Ser—Asp—Cys—Ser—Thr—Cys—Phe—Val—Ser—Gln—Ser—Gly.
                                              |                |
                                              S————————————————S

5. A pharmaceutical composition comprising a therapeutically effective amount of an isolated or purified therapeutically effective hPCSK9 polypeptide of claim 2, and a pharmaceutically acceptable carrier.

6. A method of preventing or treating hypercholesterolemia comprising administering to a subject in need thereof at least one of an isolated or purified therapeutically effective hPCSK9 polypeptide of claim 2, or combinations thereof.

7. The method of claim 6, further comprising administering a HMG-CoA reductase inhibitors (statin).

8. A kit for use for the prevention or the treatment of hypercholesterolemia in a subject in need thereof, the kit comprising:
an isolated or purified therapeutically effective hPCSK9 polypeptide consisting of the amino acid sequence of any one of SEQ ID NOs 42 to 47, and SEQ ID NO:56 and
instructions on how to use the kit.

9. The kit of claim 8, wherein the isolated or purified therapeutically effective hPCSK9 polypeptide is consisting of the amino acid sequence of any one of SEQ ID NO: 42, SEQ ID NO: 43, SEQ ID NO: 47, SEQ ID NO: 56 or combinations thereof.

10. The kit of claim 9, wherein the isolated or purified therapeutically effective hPCSK9 polypeptides is consisting of the combination of the amino acid sequence SEQ ID NO: 36 and SEQ ID NO: 42 or SEQ ID NO: 36 and SEQ ID NO: 47.

11. The kit of claim 8, comprising
an isolated or purified therapeutically effective hPCSK9 polypeptide consisting the amino acid sequence:

Gly—Glu—Asp—Ile—Ile—Gly—Ala—Ser—Ser—Asp—Cys—Ser—Thr—Cys—Phe—Val—Ser—Gln—Ser—Gly.
                                              |                |
                                              S————————————————S

12. The kit of claim 8, further comprising a HMG-CoA reductase inhibitors (statin).

13. A pharmaceutical composition comprising a therapeutically effective amount of an isolated or purified therapeutically effective hPCSK9 polypeptide of claim 4, and a pharmaceutically acceptable carrier.

* * * * *

SEQUENCE LISTING

```
<160> NUMBER OF SEQ ID NOS: 58

<210> SEQ ID NO 1
<211> LENGTH: 15
<212> TYPE: PRT
<213> ORGANISM: Homo sapiens

<400> SEQUENCE: 1

Ser Ile Pro Trp Asn Leu Glu Arg Ile Thr Pro Pro Arg Tyr Arg
1               5                   10                  15

<210> SEQ ID NO 2
<211> LENGTH: 15
<212> TYPE: PRT
<213> ORGANISM: Homo sapiens

<400> SEQUENCE: 2

Leu Glu Arg Ile Thr Pro Pro Arg Tyr Arg Ala Asp Glu Tyr Gln
1               5                   10                  15

<210> SEQ ID NO 3
<211> LENGTH: 15
<212> TYPE: PRT
<213> ORGANISM: Homo sapiens

<400> SEQUENCE: 3
```

-continued

Pro Pro Arg Tyr Arg Ala Asp Glu Tyr Gln Pro Pro Asp Gly Gly
1               5                   10                  15

<210> SEQ ID NO 4
<211> LENGTH: 15
<212> TYPE: PRT
<213> ORGANISM: Homo sapiens

<400> SEQUENCE: 4

Ala Asp Glu Tyr Gln Pro Pro Asp Gly Gly Ser Leu Val Glu Val
1               5                   10                  15

<210> SEQ ID NO 5
<211> LENGTH: 15
<212> TYPE: PRT
<213> ORGANISM: Homo sapiens

<400> SEQUENCE: 5

Pro Pro Asp Gly Gly Ser Leu Val Glu Val Tyr Leu Leu Asp Thr
1               5                   10                  15

<210> SEQ ID NO 6
<211> LENGTH: 15
<212> TYPE: PRT
<213> ORGANISM: Homo sapiens

<400> SEQUENCE: 6

Ser Leu Val Glu Val Tyr Leu Leu Asp Thr Ser Ile Gln Ser Asp
1               5                   10                  15

<210> SEQ ID NO 7
<211> LENGTH: 15
<212> TYPE: PRT
<213> ORGANISM: Homo sapiens

<400> SEQUENCE: 7

Tyr Leu Leu Asp Thr Ser Ile Gln Ser Asp His Arg Glu Ile Glu
1               5                   10                  15

<210> SEQ ID NO 8
<211> LENGTH: 15
<212> TYPE: PRT
<213> ORGANISM: Homo sapiens

<400> SEQUENCE: 8

Ser Ile Gln Ser Asp His Arg Glu Ile Glu Gly Arg Val Met Val
1               5                   10                  15

<210> SEQ ID NO 9
<211> LENGTH: 15
<212> TYPE: PRT
<213> ORGANISM: Homo sapiens

<400> SEQUENCE: 9

His Arg Glu Ile Glu Gly Arg Val Met Val Thr Asp Phe Glu Asn
1               5                   10                  15

<210> SEQ ID NO 10
<211> LENGTH: 15
<212> TYPE: PRT
<213> ORGANISM: Homo sapiens

<400> SEQUENCE: 10

Gly Arg Val Met Val Thr Asp Phe Glu Asn Val Pro Glu Glu Asp
1               5                   10                  15

<210> SEQ ID NO 11
<211> LENGTH: 15
<212> TYPE: PRT
<213> ORGANISM: Homo sapiens

<400> SEQUENCE: 11

Thr Asp Phe Glu Asn Val Pro Glu Glu Asp Gly Thr Arg Phe His
1               5                   10                  15

<210> SEQ ID NO 12
<211> LENGTH: 15
<212> TYPE: PRT
<213> ORGANISM: Homo sapiens

<400> SEQUENCE: 12

Val Pro Glu Glu Asp Gly Thr Arg Phe His Arg Gln Ala Ser Lys
1               5                   10                  15

<210> SEQ ID NO 13
<211> LENGTH: 15
<212> TYPE: PRT
<213> ORGANISM: Homo sapiens

<400> SEQUENCE: 13

Gly Thr Arg Phe His Arg Gln Ala Ser Lys Cys Asp Ser His Gly
1               5                   10                  15

<210> SEQ ID NO 14
<211> LENGTH: 15
<212> TYPE: PRT
<213> ORGANISM: Homo sapiens

<400> SEQUENCE: 14

Arg Gln Ala Ser Lys Cys Asp Ser His Gly Thr His Leu Ala Gly
1               5                   10                  15

<210> SEQ ID NO 15
<211> LENGTH: 15
<212> TYPE: PRT
<213> ORGANISM: Homo sapiens

<400> SEQUENCE: 15

Cys Asp Ser His Gly Thr His Leu Ala Gly Val Val Ser Gly Arg
1               5                   10                  15

<210> SEQ ID NO 16
<211> LENGTH: 15
<212> TYPE: PRT
<213> ORGANISM: Homo sapiens

<400> SEQUENCE: 16

Thr His Leu Ala Gly Val Val Ser Gly Arg Asp Ala Gly Val Ala
1               5                   10                  15

<210> SEQ ID NO 17
<211> LENGTH: 15
<212> TYPE: PRT
<213> ORGANISM: Homo sapiens

<400> SEQUENCE: 17

Val Val Ser Gly Arg Asp Ala Gly Val Ala Lys Gly Ala Ser Met
1               5                   10                  15

-continued

```
<210> SEQ ID NO 18
<211> LENGTH: 15
<212> TYPE: PRT
<213> ORGANISM: Homo sapiens

<400> SEQUENCE: 18

Asp Ala Gly Val Ala Lys Gly Ala Ser Met Arg Ser Leu Arg Val
1               5                   10                  15

<210> SEQ ID NO 19
<211> LENGTH: 15
<212> TYPE: PRT
<213> ORGANISM: Homo sapiens

<400> SEQUENCE: 19

Lys Gly Ala Ser Met Arg Ser Leu Arg Val Leu Asn Cys Gln Gly
1               5                   10                  15

<210> SEQ ID NO 20
<211> LENGTH: 15
<212> TYPE: PRT
<213> ORGANISM: Homo sapiens

<400> SEQUENCE: 20

Arg Ser Leu Arg Val Leu Asn Cys Gln Gly Lys Gly Thr Val Ser
1               5                   10                  15

<210> SEQ ID NO 21
<211> LENGTH: 15
<212> TYPE: PRT
<213> ORGANISM: Homo sapiens

<400> SEQUENCE: 21

Leu Asn Cys Gln Gly Lys Gly Thr Val Ser Gly Thr Leu Ile Gly
1               5                   10                  15

<210> SEQ ID NO 22
<211> LENGTH: 15
<212> TYPE: PRT
<213> ORGANISM: Homo sapiens

<400> SEQUENCE: 22

Lys Gly Thr Val Ser Gly Thr Leu Ile Gly Leu Glu Phe Ile Arg
1               5                   10                  15

<210> SEQ ID NO 23
<211> LENGTH: 15
<212> TYPE: PRT
<213> ORGANISM: Homo sapiens

<400> SEQUENCE: 23

Gly Thr Leu Ile Gly Leu Glu Phe Ile Arg Lys Ser Gln Leu Val
1               5                   10                  15

<210> SEQ ID NO 24
<211> LENGTH: 15
<212> TYPE: PRT
<213> ORGANISM: Homo sapiens

<400> SEQUENCE: 24

Leu Glu Phe Ile Arg Lys Ser Gln Leu Val Gln Pro Val Gly Pro
1               5                   10                  15

<210> SEQ ID NO 25
<211> LENGTH: 15
```

-continued

```
<212> TYPE: PRT
<213> ORGANISM: Homo sapiens

<400> SEQUENCE: 25

Lys Ser Gln Leu Val Gln Pro Val Gly Pro Leu Val Val Leu Leu
1               5                   10                  15

<210> SEQ ID NO 26
<211> LENGTH: 15
<212> TYPE: PRT
<213> ORGANISM: Homo sapiens

<400> SEQUENCE: 26

Gln Pro Val Gly Pro Leu Val Val Leu Leu Pro Leu Ala Gly Gly
1               5                   10                  15

<210> SEQ ID NO 27
<211> LENGTH: 15
<212> TYPE: PRT
<213> ORGANISM: Homo sapiens

<400> SEQUENCE: 27

Leu Val Val Leu Leu Pro Leu Ala Gly Gly Tyr Ser Arg Val Leu
1               5                   10                  15

<210> SEQ ID NO 28
<211> LENGTH: 15
<212> TYPE: PRT
<213> ORGANISM: Homo sapiens

<400> SEQUENCE: 28

Pro Leu Ala Gly Gly Tyr Ser Arg Val Leu Asn Ala Ala Cys Gln
1               5                   10                  15

<210> SEQ ID NO 29
<211> LENGTH: 15
<212> TYPE: PRT
<213> ORGANISM: Homo sapiens

<400> SEQUENCE: 29

Tyr Ser Arg Val Leu Asn Ala Ala Cys Gln Arg Leu Ala Arg Ala
1               5                   10                  15

<210> SEQ ID NO 30
<211> LENGTH: 15
<212> TYPE: PRT
<213> ORGANISM: Homo sapiens

<400> SEQUENCE: 30

Asn Ala Ala Cys Gln Arg Leu Ala Arg Ala Gly Val Val Leu Val
1               5                   10                  15

<210> SEQ ID NO 31
<211> LENGTH: 15
<212> TYPE: PRT
<213> ORGANISM: Homo sapiens

<400> SEQUENCE: 31

Arg Leu Ala Arg Ala Gly Val Val Leu Val Thr Ala Ala Gly Asn
1               5                   10                  15

<210> SEQ ID NO 32
<211> LENGTH: 15
<212> TYPE: PRT
<213> ORGANISM: Homo sapiens
```

-continued

<400> SEQUENCE: 32

Gly Val Val Leu Val Thr Ala Ala Gly Asn Phe Arg Asp Asp Ala
1               5                   10                  15

<210> SEQ ID NO 33
<211> LENGTH: 15
<212> TYPE: PRT
<213> ORGANISM: Homo sapiens

<400> SEQUENCE: 33

Thr Ala Ala Gly Asn Phe Arg Asp Asp Ala Cys Leu Tyr Ser Pro
1               5                   10                  15

<210> SEQ ID NO 34
<211> LENGTH: 15
<212> TYPE: PRT
<213> ORGANISM: Homo sapiens

<400> SEQUENCE: 34

Phe Arg Asp Asp Ala Cys Leu Tyr Ser Pro Ala Ser Ala Pro Glu
1               5                   10                  15

<210> SEQ ID NO 35
<211> LENGTH: 15
<212> TYPE: PRT
<213> ORGANISM: Homo sapiens

<400> SEQUENCE: 35

Cys Leu Tyr Ser Pro Ala Ser Ala Pro Glu Val Ile Thr Val Gly
1               5                   10                  15

<210> SEQ ID NO 36
<211> LENGTH: 15
<212> TYPE: PRT
<213> ORGANISM: Homo sapiens

<400> SEQUENCE: 36

Ala Ser Ala Pro Glu Val Ile Thr Val Gly Ala Thr Asn Ala Gln
1               5                   10                  15

<210> SEQ ID NO 37
<211> LENGTH: 15
<212> TYPE: PRT
<213> ORGANISM: Homo sapiens

<400> SEQUENCE: 37

Val Ile Thr Val Gly Ala Thr Asn Ala Gln Asp Gln Pro Val Thr
1               5                   10                  15

<210> SEQ ID NO 38
<211> LENGTH: 15
<212> TYPE: PRT
<213> ORGANISM: Homo sapiens

<400> SEQUENCE: 38

Ala Thr Asn Ala Gln Asp Gln Pro Val Thr Leu Gly Thr Leu Gly
1               5                   10                  15

<210> SEQ ID NO 39
<211> LENGTH: 15
<212> TYPE: PRT
<213> ORGANISM: Homo sapiens

<400> SEQUENCE: 39

```
Asp Gln Pro Val Thr Leu Gly Thr Leu Gly Thr Asn Phe Gly Arg
1               5                   10                  15
```

<210> SEQ ID NO 40
<211> LENGTH: 15
<212> TYPE: PRT
<213> ORGANISM: Homo sapiens

<400> SEQUENCE: 40

```
Leu Gly Thr Leu Gly Thr Asn Phe Gly Arg Cys Val Asp Leu Phe
1               5                   10                  15
```

<210> SEQ ID NO 41
<211> LENGTH: 15
<212> TYPE: PRT
<213> ORGANISM: Homo sapiens

<400> SEQUENCE: 41

```
Thr Asn Phe Gly Arg Cys Val Asp Leu Phe Ala Pro Gly Glu Asp
1               5                   10                  15
```

<210> SEQ ID NO 42
<211> LENGTH: 15
<212> TYPE: PRT
<213> ORGANISM: Homo sapiens

<400> SEQUENCE: 42

```
Cys Val Asp Leu Phe Ala Pro Gly Glu Asp Ile Ile Gly Ala Ser
1               5                   10                  15
```

<210> SEQ ID NO 43
<211> LENGTH: 15
<212> TYPE: PRT
<213> ORGANISM: Homo sapiens

<400> SEQUENCE: 43

```
Ala Pro Gly Glu Asp Ile Ile Gly Ala Ser Ser Asp Cys Ser Thr
1               5                   10                  15
```

<210> SEQ ID NO 44
<211> LENGTH: 15
<212> TYPE: PRT
<213> ORGANISM: Homo sapiens

<400> SEQUENCE: 44

```
Ile Ile Gly Ala Ser Ser Asp Cys Ser Thr Cys Phe Val Ser Gln
1               5                   10                  15
```

<210> SEQ ID NO 45
<211> LENGTH: 15
<212> TYPE: PRT
<213> ORGANISM: Homo sapiens

<400> SEQUENCE: 45

```
Ser Asp Cys Ser Thr Cys Phe Val Ser Gln Ser Gly Thr Ser Gln
1               5                   10                  15
```

<210> SEQ ID NO 46
<211> LENGTH: 15
<212> TYPE: PRT
<213> ORGANISM: Homo sapiens

<400> SEQUENCE: 46

```
Cys Phe Val Ser Gln Ser Gly Thr Ser Gln Ala Ala Ala His Val
```

```
1               5                   10                  15
```

<210> SEQ ID NO 47
<211> LENGTH: 15
<212> TYPE: PRT
<213> ORGANISM: Homo sapiens

<400> SEQUENCE: 47

```
Ser Gly Thr Ser Gln Ala Ala His Val Ala Gly Ile Ala Ala
1               5                   10                  15
```

<210> SEQ ID NO 48
<211> LENGTH: 15
<212> TYPE: PRT
<213> ORGANISM: Homo sapiens

<400> SEQUENCE: 48

```
Ala Ala Ala His Val Ala Gly Ile Ala Ala Met Met Leu Ser Ala
1               5                   10                  15
```

<210> SEQ ID NO 49
<211> LENGTH: 15
<212> TYPE: PRT
<213> ORGANISM: Homo sapiens

<400> SEQUENCE: 49

```
Ala Gly Ile Ala Ala Met Met Leu Ser Ala Glu Pro Glu Leu Thr
1               5                   10                  15
```

<210> SEQ ID NO 50
<211> LENGTH: 15
<212> TYPE: PRT
<213> ORGANISM: Homo sapiens

<400> SEQUENCE: 50

```
Met Met Leu Ser Ala Glu Pro Glu Leu Thr Leu Ala Glu Leu Arg
1               5                   10                  15
```

<210> SEQ ID NO 51
<211> LENGTH: 15
<212> TYPE: PRT
<213> ORGANISM: Homo sapiens

<400> SEQUENCE: 51

```
Glu Pro Glu Leu Thr Leu Ala Glu Leu Arg Gln Arg Leu Ile His
1               5                   10                  15
```

<210> SEQ ID NO 52
<211> LENGTH: 268
<212> TYPE: PRT
<213> ORGANISM: Homo sapiens

<400> SEQUENCE: 52

```
Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
            20                  25                  30

Leu Asp Thr Ser Ile Gln Ser Asp His Arg Glu Ile Glu Gly Arg Val
        35                  40                  45

Met Val Thr Asp Phe Glu Asn Val Pro Glu Glu Asp Gly Thr Arg Phe
    50                  55                  60

His Arg Gln Ala Ser Lys Cys Asp Ser His Gly Thr His Leu Ala Gly
65                  70                  75                  80
```

```
Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Gly Tyr Ser Arg Val
    130                 135                 140

Leu Asn Ala Ala Cys Gln Arg Leu Ala Arg Ala Gly Val Val Leu Val
145                 150                 155                 160

Thr Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
        195                 200                 205

Leu Phe Ala Pro Gly Glu Asp Ile Ile Gly Ala Ser Ser Asp Cys Ser
    210                 215                 220

Thr Cys Phe Val Ser Gln Ser Gly Thr Ser Gln Ala Ala Ala His Val
225                 230                 235                 240

Ala Gly Ile Ala Ala Met Met Leu Ser Ala Glu Pro Glu Leu Thr Leu
                245                 250                 255

Ala Glu Leu Arg Gln Arg Leu Ile His Phe Ser Ala
            260                 265

<210> SEQ ID NO 53
<211> LENGTH: 670
<212> TYPE: PRT
<213> ORGANISM: Homo sapiens

<400> SEQUENCE: 53

Asp Tyr Lys Asp Asp Asp Asp Lys Gln Glu Asp Glu Asp Gly Asp Tyr
1               5                   10                  15

Glu Glu Leu Val Leu Ala Leu Arg Ser Glu Glu Asp Gly Leu Ala Glu
            20                  25                  30

Ala Pro Glu His Gly Thr Thr Ala Thr Phe His Arg Cys Ala Lys Asp
        35                  40                  45

Pro Trp Arg Leu Pro Gly Thr Tyr Val Val Val Leu Lys Glu Glu Thr
    50                  55                  60

His Leu Ser Gln Ser Glu Arg Thr Ala Arg Arg Leu Gln Ala Gln Ala
65                  70                  75                  80

Ala Arg Arg Gly Tyr Leu Thr Lys Ile Leu His Val Phe His Gly Leu
                85                  90                  95

Leu Pro Gly Phe Leu Val Lys Met Ser Gly Asp Leu Leu Glu Leu Ala
            100                 105                 110

Leu Lys Leu Pro His Val Asp Tyr Ile Glu Glu Asp Ser Ser Val Phe
        115                 120                 125

Ala Gln Ser Ile Pro Trp Asn Leu Glu Arg Ile Thr Pro Pro Arg Tyr
    130                 135                 140

Arg Ala Asp Glu Tyr Gln Pro Pro Asp Gly Gly Ser Leu Val Glu Val
145                 150                 155                 160

Tyr Leu Leu Asp Thr Ser Ile Gln Ser Asp His Arg Glu Ile Glu Gly
                165                 170                 175

Arg Val Met Val Thr Asp Phe Glu Asn Val Pro Glu Glu Asp Gly Thr
```

```
                180                 185                 190
Arg Phe His Arg Gln Ala Ser Lys Cys Asp Ser His Gly Thr His Leu
            195                 200                 205
Ala Gly Val Val Ser Gly Arg Asp Ala Gly Val Ala Lys Gly Ala Ser
            210                 215                 220
Met Arg Ser Leu Arg Val Leu Asn Cys Gln Lys Gly Thr Val Ser
225                 230                 235                 240
Gly Thr Leu Ile Gly Leu Glu Phe Ile Arg Lys Ser Gln Leu Val Gln
                245                 250                 255
Pro Val Gly Pro Leu Val Val Leu Pro Leu Ala Gly Gly Tyr Ser
            260                 265                 270
Arg Val Leu Asn Ala Ala Cys Gln Arg Leu Ala Arg Ala Gly Val Val
            275                 280                 285
Leu Val Thr Ala Ala Gly Asn Phe Arg Asp Asp Ala Cys Leu Tyr Ser
            290                 295                 300
Pro Ala Ser Ala Pro Glu Val Ile Thr Val Gly Ala Thr Asn Ala Gln
305                 310                 315                 320
Asp Gln Pro Val Thr Leu Gly Thr Leu Gly Thr Asn Phe Gly Arg Cys
                325                 330                 335
Val Asp Leu Phe Ala Pro Gly Glu Asp Ile Ile Gly Ala Ser Ser Asp
            340                 345                 350
Cys Ser Thr Cys Phe Val Ser Gln Ser Gly Thr Ser Gln Ala Ala Ala
            355                 360                 365
His Val Ala Gly Ile Ala Ala Met Met Leu Ser Ala Glu Pro Glu Leu
            370                 375                 380
Thr Leu Ala Glu Leu Arg Gln Arg Leu Ile His Phe Ser Ala Lys Asp
385                 390                 395                 400
Val Ile Asn Glu Ala Trp Phe Pro Glu Asp Gln Arg Val Leu Thr Pro
                405                 410                 415
Asn Leu Val Ala Ala Leu Pro Pro Ser Thr His Gly Ala Gly Trp Gln
            420                 425                 430
Leu Phe Cys Arg Thr Val Trp Ser Ala His Ser Gly Pro Thr Arg Met
            435                 440                 445
Ala Thr Ala Val Ala Arg Cys Ala Pro Asp Glu Glu Leu Leu Ser Cys
            450                 455                 460
Ser Ser Phe Ser Arg Ser Gly Lys Arg Arg Gly Glu Arg Met Glu Ala
465                 470                 475                 480
Gln Gly Gly Lys Leu Val Cys Arg Ala His Asn Ala Phe Gly Gly Glu
                485                 490                 495
Gly Val Tyr Ala Ile Ala Arg Cys Cys Leu Leu Pro Gln Ala Asn Cys
            500                 505                 510
Ser Val His Thr Ala Pro Pro Ala Glu Ala Ser Met Gly Thr Arg Val
            515                 520                 525
His Cys His Gln Gln Gly His Val Leu Thr Gly Cys Ser Ser His Trp
            530                 535                 540
Glu Val Glu Asp Leu Gly Thr His Lys Pro Pro Val Leu Arg Pro Arg
545                 550                 555                 560
Gly Gln Pro Asn Gln Cys Val Gly His Arg Glu Ala Ser Ile His Ala
                565                 570                 575
Ser Cys Cys His Ala Pro Gly Leu Glu Cys Lys Val Lys Glu His Gly
            580                 585                 590
Ile Pro Ala Pro Gln Glu Gln Val Thr Val Ala Cys Glu Glu Gly Trp
            595                 600                 605
```

-continued

```
Thr Leu Thr Gly Cys Ser Ala Leu Pro Gly Thr Ser His Val Leu Gly
    610                 615                 620

Ala Tyr Ala Val Asp Asn Thr Cys Val Val Arg Ser Arg Asp Val Ser
625                 630                 635                 640

Thr Thr Gly Ser Thr Ser Glu Gly Ala Val Thr Ala Val Ala Ile Cys
                645                 650                 655

Cys Arg Ser Arg His Leu Ala Gln Ala Ser Gln Glu Leu Gln
                660                 665                 670

<210> SEQ ID NO 54
<211> LENGTH: 35
<212> TYPE: PRT
<213> ORGANISM: Homo sapiens

<400> SEQUENCE: 54

Cys Leu Tyr Ser Pro Ala Ser Ala Pro Glu Val Ile Thr Val Gly Ala
1               5                   10                  15

Thr Asn Ala Gln Asp Gln Pro Val Thr Leu Gly Thr Leu Gly Thr Asn
                20                  25                  30

Phe Gly Arg
        35

<210> SEQ ID NO 55
<211> LENGTH: 25
<212> TYPE: PRT
<213> ORGANISM: Homo sapiens

<400> SEQUENCE: 55

Ile Ile Gly Ala Ser Ser Asp Cys Ser Thr Cys Phe Val Ser Gln Ser
1               5                   10                  15

Gly Thr Ser Gln Ala Ala Ala His Val
                20                  25

<210> SEQ ID NO 56
<211> LENGTH: 20
<212> TYPE: PRT
<213> ORGANISM: Homo sapiens

<400> SEQUENCE: 56

Gly Glu Asp Ile Ile Gly Ala Ser Ser Asp Cys Ser Thr Cys Phe Val
1               5                   10                  15

Ser Gln Ser Gly
            20

<210> SEQ ID NO 57
<211> LENGTH: 20
<212> TYPE: PRT
<213> ORGANISM: Homo sapiens

<400> SEQUENCE: 57

Gly Glu Asp Ile Ile Gly Ala Ser Ser Tyr Cys Ser Thr Cys Phe Val
1               5                   10                  15

Ser Gln Ser Gly
            20

<210> SEQ ID NO 58
<211> LENGTH: 40
<212> TYPE: PRT
<213> ORGANISM: Homo sapiens

<400> SEQUENCE: 58
```

```
Cys Val Asp Leu Phe Ala Pro Gly Glu Asp Ile Ile Gly Ala Ser Ser
1               5                  10                  15

Asp Cys Ser Thr Cys Phe Val Ser Gln Ser Gly Thr Ser Gln Ala Ala
                20                  25                  30

Ala His Val Ala Gly Ile Ala Ala
        35                  40
```